(12) United States Patent
Rubbert et al.

(10) Patent No.: US 7,068,836 B1
(45) Date of Patent: Jun. 27, 2006

(54) SYSTEM AND METHOD FOR MAPPING A SURFACE

(75) Inventors: Rudger Rubbert, Berlin (DE); Peer Sporbert, Berlin (DE); Thomas Weise, Berlin (DE)

(73) Assignee: OraMetrix, Inc., Richardson, TX (US)

( * ) Notice: Subject to any disclaimer, the term of this patent is extended or adjusted under 35 U.S.C. 154(b) by 0 days.

(21) Appl. No.: 09/560,584

(22) Filed: Apr. 28, 2000

(51) Int. Cl.
*G06K 9/00* (2006.01)

(52) U.S. Cl. ............... 382/154; 382/285; 348/66; 356/12

(58) Field of Classification Search ........... 382/108, 382/154, 173, 174, 181, 285; 348/136, 143, 348/144, 66; 356/601–605, 618, 610, 12; 345/419
See application file for complete search history.

(56) References Cited

U.S. PATENT DOCUMENTS

| | | | |
|---|---|---|---|
| 4,286,852 A | 9/1981 | Stern et al. ............ 396/106 |
| 4,294,544 A | 10/1981 | Altschuler et al. ........ 356/610 |
| 4,508,452 A | 4/1985 | DiMatteo et al. ......... 356/610 |
| 4,575,805 A | 3/1986 | Moermann et al. |
| 4,616,121 A | 10/1986 | Clocksin et al. ...... 219/124.34 |
| 4,634,278 A | 1/1987 | Ross et al. ............. 356/376 |
| 4,745,469 A | 5/1988 | Waldecker et al. ......... 348/94 |
| 4,935,635 A | 6/1990 | O'Harra ............. 250/559.06 |
| 5,011,405 A | 4/1991 | Lemchen |
| 5,027,281 A | 6/1991 | Rekow et al. ......... 364/474.24 |
| 5,028,799 A | 7/1991 | Chen et al. ............... 250/561 |
| 5,098,426 A | 3/1992 | Sklar et al. ................. 606/5 |
| 5,131,844 A | 7/1992 | Marinaccio et al. .......... 433/72 |
| 5,214,686 A | 5/1993 | Webber .................... 378/38 |
| 5,238,404 A | 8/1993 | Andreiko |
| 5,243,665 A | 9/1993 | Maney et al. ............. 382/152 |
| 5,347,454 A | 9/1994 | Mushabac ................. 433/214 |
| 5,368,478 A | 11/1994 | Andreiko et al. |
| 5,395,238 A | 3/1995 | Andreiko et al. |

(Continued)

FOREIGN PATENT DOCUMENTS

JP      H9-21620      1/1997

(Continued)

OTHER PUBLICATIONS

Dianne Rekow article, "Computer-aided design and manufacturing in dentistry: A review of the state of the art", *Journal of Prosthetic Dentistry*, vol. 58, Oct. 1987, pp. 512-516.

(Continued)

*Primary Examiner*—Samir Ahmed
(74) *Attorney, Agent, or Firm*—McDonnell Boehnen Hulbert & Berghoff LLP

(57) ABSTRACT

In accordance with a specific embodiment of the present invention, an image is projected upon a surface. The image can include a pattern having a plurality of individual shapes used to measure and map the surface. The plurality of individual shapes include features that are detectable in a direction parallel to the plane formed by a projection axis of the projected shapes and a point associated with a view axis. The image further comprises a feature containing an encoding information for identifying the plurality of shapes individually. The feature containing encoding information can be a separate feature from each of the plurality of individual shapes, or may be a feature integral to the plurality of individual shapes. The feature containing encoding information is oriented such that the encoding information is retrieved along a line perpendicular to a plane formed by the projection axis and the point along the view axis. The use of the feature is used to perform multiframe reference independent scanning.

30 Claims, 31 Drawing Sheets

U.S. PATENT DOCUMENTS

| | | | |
|---|---|---|---|
| 5,431,562 A | 7/1995 | Andreiko et al. | |
| 5,447,432 A | 9/1995 | Andreiko et al. | |
| 5,454,717 A | 10/1995 | Andreiko et al. | |
| 5,456,600 A | 10/1995 | Andreiko et al. | |
| 5,464,349 A | 11/1995 | Andreiko et al. | |
| 5,474,448 A | 12/1995 | Andreiko et al. | |
| 5,513,276 A | 4/1996 | Theodoracatos | 382/154 |
| 5,518,397 A | 5/1996 | Andreiko et al. | |
| 5,533,895 A | 7/1996 | Andreiko et al. | |
| 5,542,842 A | 8/1996 | Andreiko et al. | |
| 5,604,817 A | 2/1997 | Massen et al. | 382/120 |
| 5,615,003 A | 3/1997 | Hermary et al. | 356/3.03 |
| 5,618,176 A | 4/1997 | Andreiko et al. | |
| 5,715,166 A | 2/1998 | Besl et al. | 364/474.24 |
| 5,724,435 A | 3/1998 | Malzbender | 382/103 |
| 5,742,294 A | 4/1998 | Watanabe et al. | 345/425 |
| RE35,816 E | 6/1998 | Schulz | 356/608 |
| 5,823,778 A | 10/1998 | Schmitt et al. | 433/214 |
| 5,848,115 A | 12/1998 | Little et al. | 378/4 |
| 5,880,961 A | 3/1999 | Crump | 700/112 |
| 5,886,775 A | 3/1999 | Houser et al. | 356/4.01 |
| 5,975,893 A | 11/1999 | Chishti et al. | 433/6 |
| 5,985,495 A | 11/1999 | Okumura et al. | 430/22 |
| 5,988,862 A | 11/1999 | Kacyra et al. | 703/6 |
| 5,991,437 A | 11/1999 | Migdal et al. | 382/154 |
| 6,031,941 A * | 2/2000 | Yano et al. | 382/276 |
| 6,068,482 A | 5/2000 | Snow | 433/223 |
| 6,088,695 A | 7/2000 | Kara | 707/10 |
| 6,099,314 A | 8/2000 | Kopelman et al. | 433/213 |
| 6,100,893 A | 8/2000 | Ensz et al. | 345/420 |
| 6,124,934 A | 9/2000 | Shahar et al. | 356/624 |
| 6,139,499 A | 10/2000 | Wilk | 600/443 |
| 6,167,151 A | 12/2000 | Albeck et al. | 382/154 |
| 6,201,546 B1 | 3/2001 | Bodor et al. | 345/430 |
| 6,205,716 B1 | 3/2001 | Peltz | 52/36.2 |
| 6,211,506 B1 | 4/2001 | Pryor et al. | 250/208.1 |
| 6,217,325 B1 | 4/2001 | Chishti et al. | 433/24 |
| 6,217,334 B1 | 4/2001 | Hultgren | 433/215 |
| 6,227,850 B1 | 5/2001 | Chishti et al. | 433/24 |
| 6,227,851 B1 | 5/2001 | Chishti et al. | 433/24 |
| 6,253,164 B1 | 6/2001 | Rohm et al. | 703/2 |
| 6,266,453 B1 | 7/2001 | Hibbard et al. | |
| 6,405,151 B1 | 6/2002 | Fujii et al. | |
| 6,413,084 B1 | 7/2002 | Rubbert et al. | 433/29 |
| 6,466,892 B1 | 10/2002 | Fujii et al. | |
| 6,495,848 B1 * | 12/2002 | Rubbert | 250/559.22 |
| 6,542,248 B1 * | 4/2003 | Schwarz | 356/600 |
| 6,542,249 B1 * | 4/2003 | Kofman et al. | 356/601 |
| 6,549,288 B1 * | 4/2003 | Migdal et al. | 356/603 |
| 6,553,138 B1 | 4/2003 | Rozin | |
| 6,556,783 B1 * | 4/2003 | Gelphman | 396/20 |
| 6,728,423 B1 * | 4/2004 | Rubbert et al. | 382/294 |
| 6,744,914 B1 * | 6/2004 | Rubbert et al. | 382/154 |
| 6,744,932 B1 * | 6/2004 | Rubbert et al. | 382/294 |

FOREIGN PATENT DOCUMENTS

| | | |
|---|---|---|
| JP | 2000113193 | 4/2000 |
| WO | WO9811404 | 3/1998 |

OTHER PUBLICATIONS

International Search Report dated Aug. 15, 2001, for International Application No. PCT/US01/12107 of OraMetrix, Inc.

Yee et al., "Three-Dimensional Imaging System", *Optical Engineering*, vol. 33, No. 6, pp. 2070-2075 (Jun. 1994).

U.S. Appl. No. 09/560,133, filed Apr. 28, 2000, Rubbert et al.

U.S. Appl. No. 09/560,645, filed Apr. 28, 2000, Rubbert et al.

* cited by examiner

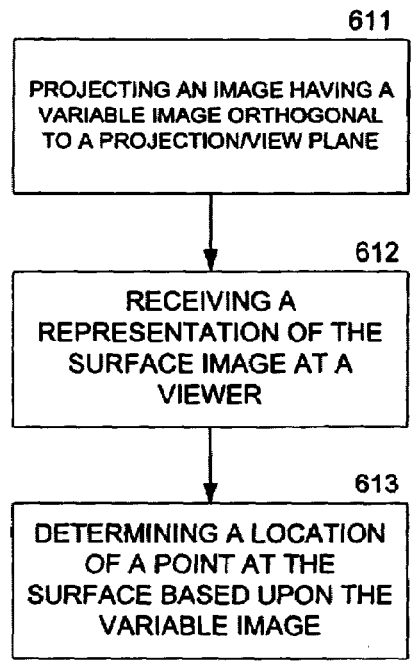
FIGURE 12
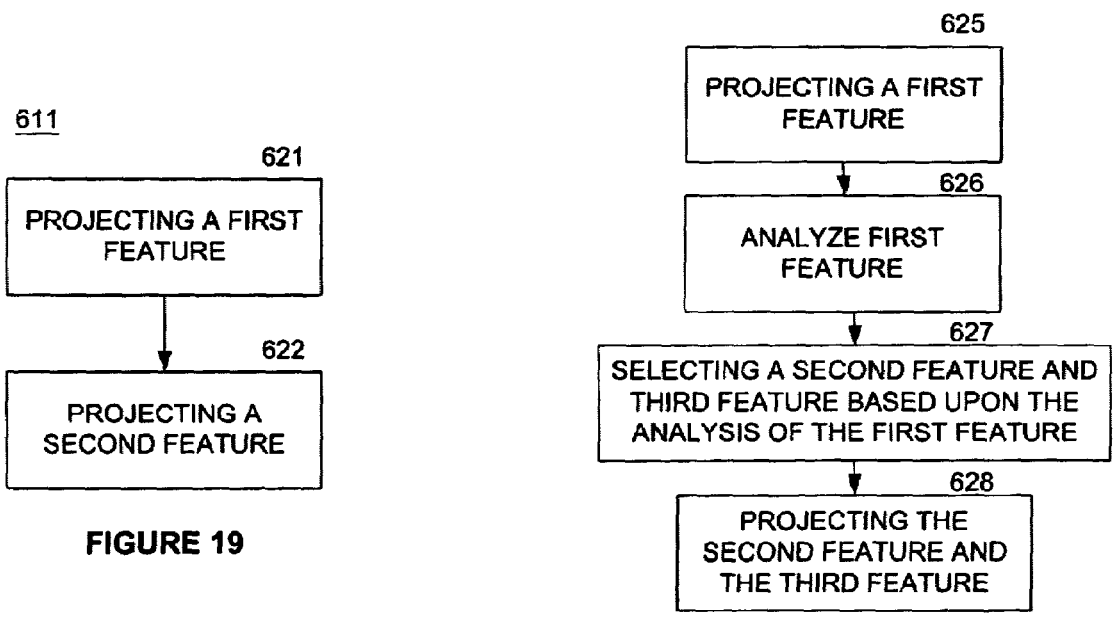
FIGURE 19
FIGURE 20

| SHAPE NUMBER | BAR CODE | COLOR | PATTERN |
|---|---|---|---|
| 0 | ❘ ❘ ❘ | RED | |
| 1 | ❘ ❘ ❙ | ORANGE | |
| 2 | ❘ ❙ ❘ | YELLOW | |
| 3 | ❘ ❙ ❙ | GREEN | |
| 4 | ❙ ❘ ❘ | BLUE | |
| 5 | ❙ ❘ ❙ | INDIGO | |
| 6 | ❙ ❙ ❘ | VIOLATE | |
| 7 | ❙ ❙ ❙ | BROWN | |

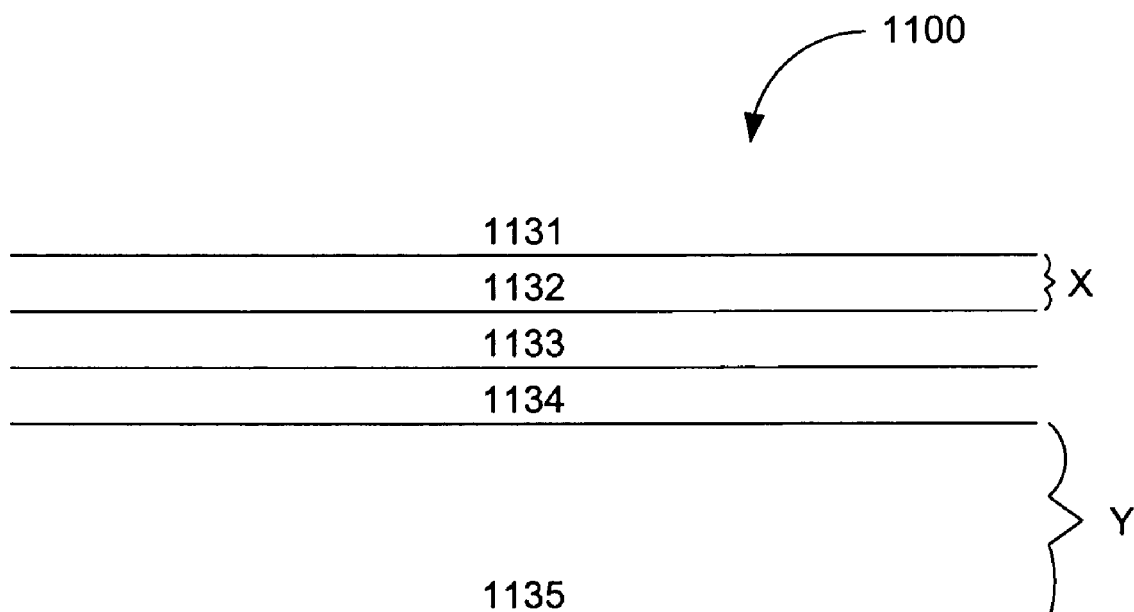
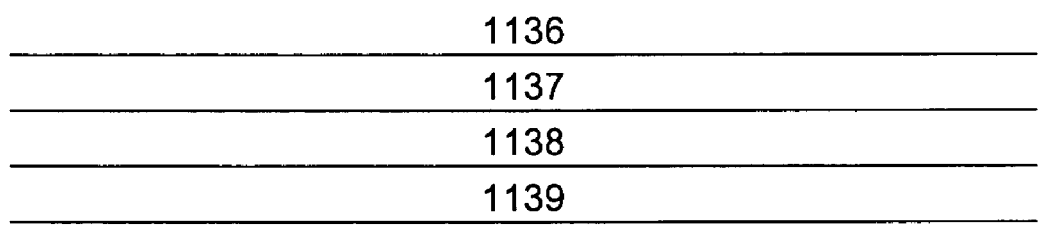
Figure 24

SYSTEM AND METHOD FOR MAPPING A SURFACE

COPENDING AND RELATED APPLICATIONS

A copending application exists having Ser. No. 09/560,645, entitled "System and Method for Mapping a Surface", having at least one inventor in common, and the same filing date as the present application.

A copending application exists having Ser. No. 09/560,133, entitled "System and Method for Mapping a Surface", having at least one inventor in common, and the same filing date as the present application.

A copending application exists having Ser. No. 09/560,644, entitled "Method and System of Scanning", having at least one inventor in common, the same filing date as the present application, and now issued as U.S. Pat. No. 6,413,084.

A copending application exists having Ser. No. 09/560,131, entitled "Method and System for Generating a Three-Dimensional Object", having at least one inventor in common, and the same filing date as the present application.

A copending application exists having Ser. No. 09/560,132, entitled "Method and System for Registering Data", having at least one inventor in common, and the same filing date as the present application.

A copending application exists having Ser. No. 09/560,583, entitled "Method and System for Registering Data", having at least one inventor in common, and the same filing date as the present application.

FIELD OF THE INVENTION

The present invention relates generally to the mapping of objects, and more specifically, to providing specific images to aid the mapping of objects.

BACKGROUND OF THE INVENTION

The use of scanning techniques to map surfaces of objects is well known. Prior art FIG. 1 illustrates an object 100 having visible surfaces 101–104. Generally, the visible surfaces 101–103 form a rectangular shape residing on top of a generally planer surface 104.

Projected onto the object 100 is an image, which includes the line 110. In operation, the image of line 110 is received by a viewing device, such as a camera, (not shown) and processed in order to determine the shape of that portion of object 100 where the line 110 resides. By moving the line 110 across the object 100, it is possible to map the entire object 100. Limitations associated with using an image comprising a single line 110 is that a significant amount of time is needed to scan the object 100 to provide an accurate map, and a fixed reference point is needed at either the scanner or the object.

FIG. 2 illustrates a prior art solution to reduce the amount of time taken to scan an object. Specifically, FIG. 2 illustrates an image including lines 121 through 125. By providing multiple lines, it is possible to scan a greater surface area at once, thus allowing for more efficient processing of data associated with the object 100. Limitations of using patterns such as are illustrated in FIG. 2 include the need for a fixed reference point, and that the surface resolution capable of being mapped can be reduced because of the potential for improper processing of data due to overlapping of the discrete portions of the image.

In order to better understand the concept of overlapping, it is helpful to understand the scanning process. Prior art FIG. 3 illustrates the shapes of FIGS. 1 and 2 from a side view such that only surface 102 is visible. For discussion purposes, the projection device (not illustrated) projects a pattern in a direction perpendicular to the surface 101 which forms the top edge of surface 102 in FIG. 3. The point from the center of the projection lens to the surface is referred to as the projection axis, the rotational axis of the projection lens, or the centerline of the projection lens. Likewise, an imaginary line from a center point of the viewing device (not shown) is refereed to as the view axis, the rotational axis of the view device, or the centerline of the view device, extends in the direction which the viewing device is oriented.

The physical relationship of the projection axis and the view axis with respect to each other is generally known. In the specific illustration of FIG. 3, the projection axis and the view axis reside in a common plane. The relationship between the projection system and the view system is physically calibrated, such that the relationship between the projector, and the view device is known. Note the term "point of reference" is to describe the reference from which a third person, such as the reader, is viewing an image. For example, for FIG. 2, the point of reference is above and to the side of the point that is formed by surfaces 101, 102, and 103.

FIG. 4 illustrates the object 100 with the image of FIG. 2 projected upon it where the point of reference is equal to the projection angle. When the point of reference is equal to the projection angle, no discontinuities appear in the projected image. In other words, the lines 121–125 appear to be straight lines upon the object 100. However, where the point of reference is equal to the projection axis, no useful data for mapping objects is obtained, because the lines appear to be undistorted.

FIG. 5 illustrates the object 100 from a point of reference equal to the view angle of FIG. 2. In FIG. 5, the surfaces 104, 103 and 101 are visible because the view axis is substantially perpendicular to the line formed by surfaces 101 and 103, and is to the right of the plane formed by surface 102, see FIG. 2, which is therefore not illustrated in FIG. 5. Because of the angle at which the image is being viewed, or received by the viewing device, the lines 121 and 122 appear to be a single continuous straight line. Likewise, line pairs 122 and 123, and 123 and 124, coincide to give the impression that they are single continuous lines. Because line 125 is projected upon a single level surface elevation, surface 104, line 125 is a continuous single line.

When the pattern of FIG. 5 is received by a processing device to perform a mapping function, the line pairs 121 and 122, 122 and 123, and 123 and 124, will be improperly interpreted as single lines. As a result, the two-tiered object illustrated in FIG. 2 may actually be mapped as a single level surface, or otherwise inaccurately displayed because the processing steps can not distinguish between the line pairs.

FIG. 6 illustrates a prior art solution for overcoming the problem described in FIG. 5. Specifically, FIG. 6 illustrates the shape 100 having an image projected upon it whereby a plurality of lines having different line widths, or thickness, are used. FIG. 7 illustrates the pattern of FIG. 6 from the same point of reference as that of FIG. 5.

As illustrated in FIG. 7, it is now possible for a processing element analyzing the received data to distinguish between the previously indistinguishable line pairs. Referring to FIG. 7, line 421 is still lined up with line 422 to form what appears to be a continuous line. However, because line 421 and line 425 have different thickness, it is now possible for an analysis of the image to determine the correct identity of the specific line segments. In other words, the analysis of the received image can now determine that line 422 projected on surface 104, and line 422 projected on surface 101 are actually a common line. Utilizing this information, the analysis of the received image can determine that a step type feature occurs on the object being scanned, resulting in the incongruity between the two segments of line 422.

While the use of varying line thickness, as illustrated in FIG. 7, assists identifying line segments, objects that have varying features of the type illustrated can still result in errors during the analysis of the received image.

FIG. 8 illustrates from a side point of reference a structure having a surface 710 with sharply varying features. The surface 710 is illustrated to be substantially perpendicular to the point of reference of FIG. 8. In addition, the object 700 has side surfaces 713 and 715, and top surfaces 711 and 712. From the point of reference of FIG. 8, the actual surfaces 711, 712, 713 and 715 are not viewed, only their edges are represented. The surface 711 is a relatively steep sloped surface, while the surface 712 is a relatively gentle sloped surface.

Further illustrated in FIG. 8 are three projected lines 721 through 723 having various widths. A first line 721 has a width of four. A second projected line 722 has a width of one. A third projected line 723 has a width of eight.

The line 721, having a width of four, is projected onto a relatively flat surface 714. Because of the angle between the projection axis and the view axis, the actual line 721 width viewed at the flat surface 714 is approximately two. If the lines 722 and 723 where also projected upon the relatively flat surface 714 their respected widths would vary by approximately the same proportion amount as that of 721, such that the thickness can be detected during the analysis steps of mapping the surface. However, because line 722 is projected onto the angled surface 711, the perspective from the viewing device along the viewing axis is such that the line 722 has a viewed width of two.

Line 722 appears to have a width of two because the steep angle of the surface 710 allows for a greater portion of the projected line 722 to be projected onto a greater area of the surface 711. It is this greater area of the surface 722 that is viewed to give the perception that the projected line 722 has a thickness of two.

In a manner opposite to how line 722 is affected by surface 711, line 723 is affected by surface 712 to give the perception that the projected line 723 having an actual width of eight, has a width of two. This occurs because the angle of the surface 712, relative to the viewing device allows the surface area with the projected line 723 to appear to have a width of two. The result of this phenomenon is further illustrated in FIG. 9.

FIG. 9 illustrates the shape 700 of FIG. 8 from the point of reference of the view axis. From the point of reference of the view axis, the lines 721–723 are projected onto the surface 714 in such a manner that the difference between the line thickness can be readily determined. Therefore, when an analysis of the surface area 714 occurs, the lines are readily discernable based upon the viewed image. However, when an analysis includes the surfaces 711 and 712, the line 722 can be erroneously identified as being line 721 because not only are the widths the same, but line 722 on surface 711 lines up with line 721 on surface 714. Likewise, the line 723, having a projected width of eight, has a viewed width of two. Therefore, during the analysis of the received images, it may not be possible to distinguish between lines 721, 722, and 723 on surfaces 711 and 712. The inability to distinguish between such lines can result in an erroneous analysis of the surfaces.

One proposed method of scanning, disclosed in foreign patent DE 198 21 611.4, used a pattern that had rows of black and white triangles and squares running parallel to a plane of triangulation. The rows used measuring features that include a digital encrypted pattern. However, when a surface being scanned causes shadowing and/or undercuts, a break in the sequence can result due to a portion of the pattern being hidden. Furthermore, the disclosed encrypted pattern is such that breaks in the sequence can result in the inability to decode the pattern, since it may not be possible to know which portion of the pattern is missing. A further limitation of the type of encoding described is that distortion can cause one encoding feature to look like another. For example, a triangle can be made to look like a square.

Therefore, a method and apparatus capable of overcoming the problems associated with the prior art mapping of objects would be advantageous.

BRIEF DESCRIPTION OF THE DRAWINGS

FIG. 12 illustrates, in flow diagram form, a method in accordance with the present invention;

FIG. 16 illustrates a table identifying various types of pattern components in accordance with the present invention;

FIG. 17 illustrates a set of unique identifiers in accordance with the present invention;

FIG. 18 illustrates a set of repeating identifiers in accordance with the present invention;

FIGS. 19–22 illustrate, in flow diagram form, a method in accordance with the present invention;

FIG. 24 illustrates an image having varying features in accordance with an embodiment of the present invention;

DETAILED DESCRIPTION OF THE DRAWINGS

In accordance with a specific embodiment of the present invention, an image is projected upon a surface. The image can include a pattern having a plurality of individual shapes used to measure and map the surface. The plurality of individual shapes include features that are detectable in a direction parallel to the plane formed by a projection axis of the projected shapes and a point associated with a view axis. The image further comprises a feature containing encoding information for identifying the plurality of shapes individually. The encoding feature varies in a direction substantially orthogonal to a plane formed by the projection axis and a point of a view axis, and can be a separate feature from each of the plurality of individual shapes, can be a feature integral to the plurality of individual shapes, and/or be displayed at different time intervals from the plurality of individual shapes. The feature containing encoding information is oriented such that the encoding information is retrieved along a line substantially perpendicular to a plane formed by the projection axis and the point along the view axis. The use of the feature is used to perform multi-frame reference independent scanning.

Figure 10:
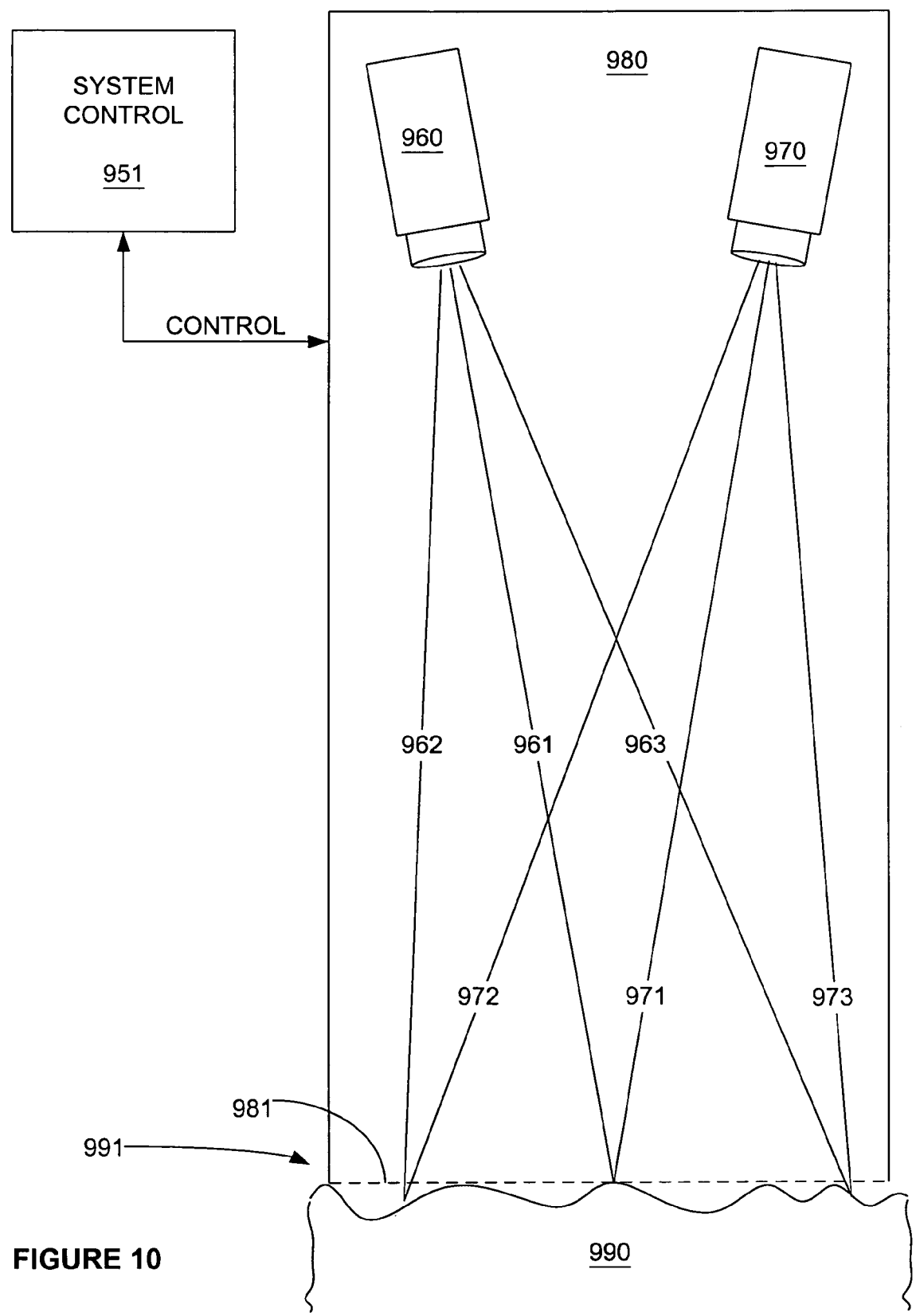
FIG. 10 illustrates a system in accordance with the present invention.
Figure 11:
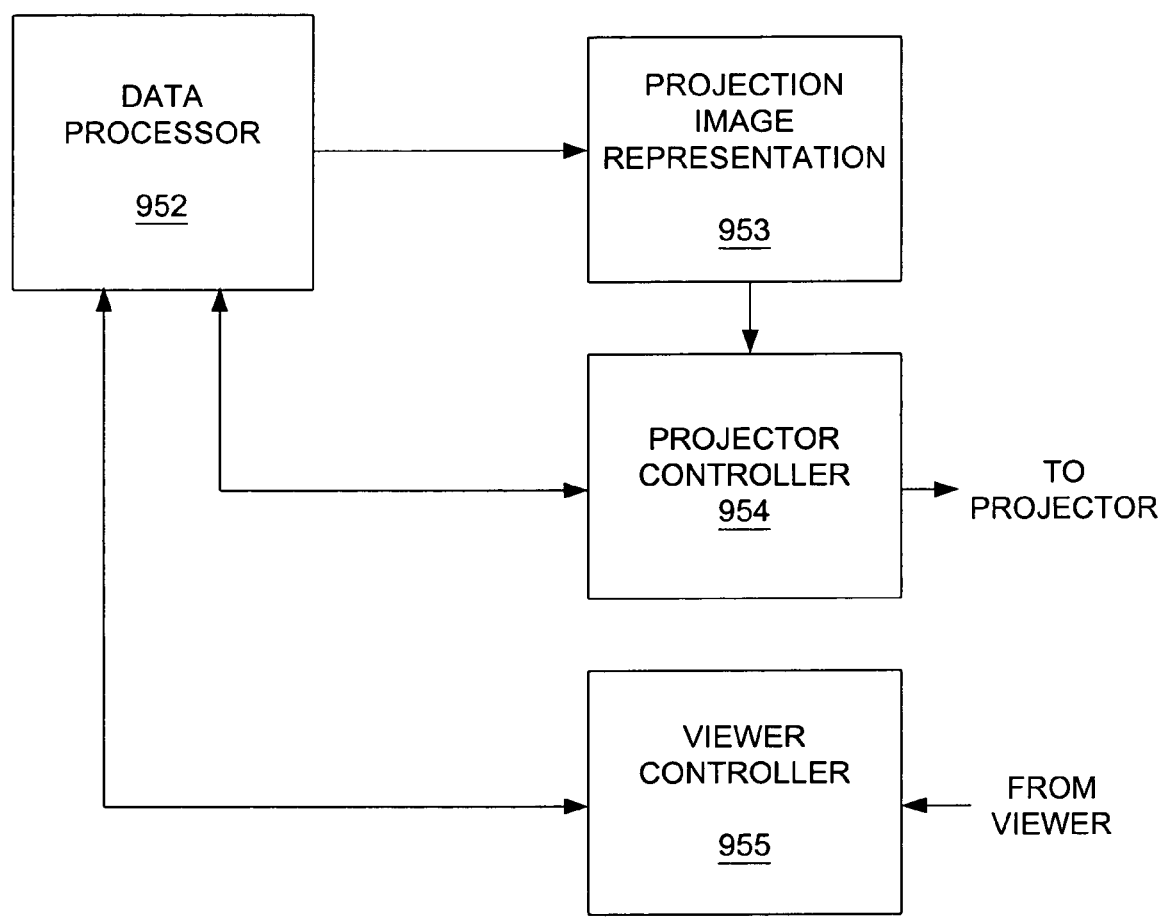
FIG. 11 illustrates a portion of the system of FIG. 10 in accordance with the present invention.

Specific embodiments of the present invention are best understood with reference to the accompanying FIGS. 10–24. FIGS. 10 and 11 represent a system for implementing a specific embodiment of the present invention, FIGS. 12, and 19–22 illustrate specific methods in accordance with the present invention, and FIGS. 13–18, 23, 24 illustrates specific implementations of the method in combination with the system.

FIG. 10 illustrates a system controller 951 that provides control signals to the scanning device 980. The scanning device 980 projects an image bound by lines 962 and 963, and retrieves, or views, the images within the reflected lines 972 and 973.

In one operation, the system controller 951 provides specific information to the scanner 980 specifying a specific image to be projected upon the surface 991 of the object 990. The reflected image is captured by the scanning device 980, which in turn provides the captured information back to the system controller 951. The captured information can be provided back to system controller 951 automatically, or can be stored within the scanning device 980 and retrieved by the system 951. The image data once received by the system controller 951 is analyzed in order to determine the shape of the surface 991. Note that the analysis of the received data can be performed either by the system controller 951, or by an external-processing device that is not shown.

Further illustrated in FIG. 10 is the scanning device 980, which includes a projecting device (projector) 960 and a viewing device (viewer) 970. The projector 960 is oriented such that the image is projected on the object 990. The projector 960 has a projection axis 961. The projection axis 961 begins at the center of the lens projecting the image and is representative of the direction of projection. Likewise, the viewer 970 has a view axis 971 that extends from the center of the lens associated with the viewer 970 and represents the direction from which images are being received.

Once the scanning device is calibrated, analysis of the received signals can be performed to map the scanned surface. One skilled in the art will recognize that the angles represented in the Figures herein are represented as such for illustrative purposes only. The actual angles and distances may vary substantially from those illustrated.

FIG. 11 illustrates in greater detail the system controller 951 of FIG. 10. The system controller 951 further includes data processor 952, a projection image representation 953, the projector controller 954, and a viewer controller 955.

The viewer controller 955 provides the interface needed to receive data from the viewer 970 representing the reflected image data. The reflected image data is received from the viewer 970 at the viewer controller 955, and subsequently provided to the data processor 952. In a similar manner, the projector controller 954 provides the interface necessary to control the projector 960. The projector controller 954 provides the projector 960 with the image to be projected in a format supported by the projector. In response, the projector 960 projects the image onto the surface of the object. The projector controller 954 receives or accesses the projection image representation 953 in order to provide the projector with the image.

In the embodiment illustrated, the projection image representation 953 is an electronic representation of the image stored in a memory location. The stored image can represent a bit mapped image, or other standard or custom protocol used to define the image to be projected by the projector 960. Where the projection image is a digital image (electrically generated), the representation can be stored in memory by data processor 952, thereby allowing the data processor 952 to modify the projection image representation, it is possible to vary the image as necessary in accordance with the present invention.

In another embodiment, the projection image representation 953 need not be present. Instead, the projection controller 954 may select one or more transparencies (not illustrated) associated with the projector 960. Such transparencies can include any combination of films, plates, or other types of retical devices that project images.

The data processor 952 controls the projection and reception of data through the controller 954 and 955 respectively.

Figure 1:
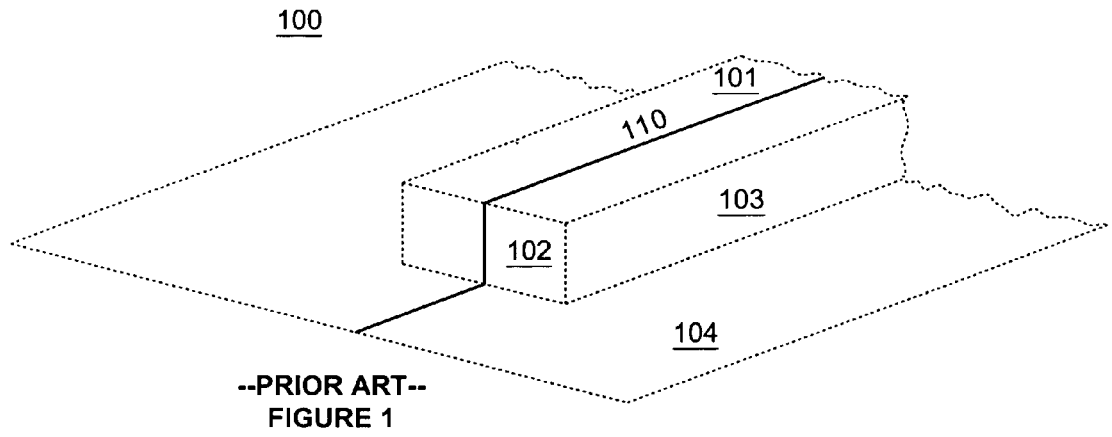
FIG. 1 illustrates an object being scanned by a single line in accordance with the prior art.
Figure 2:
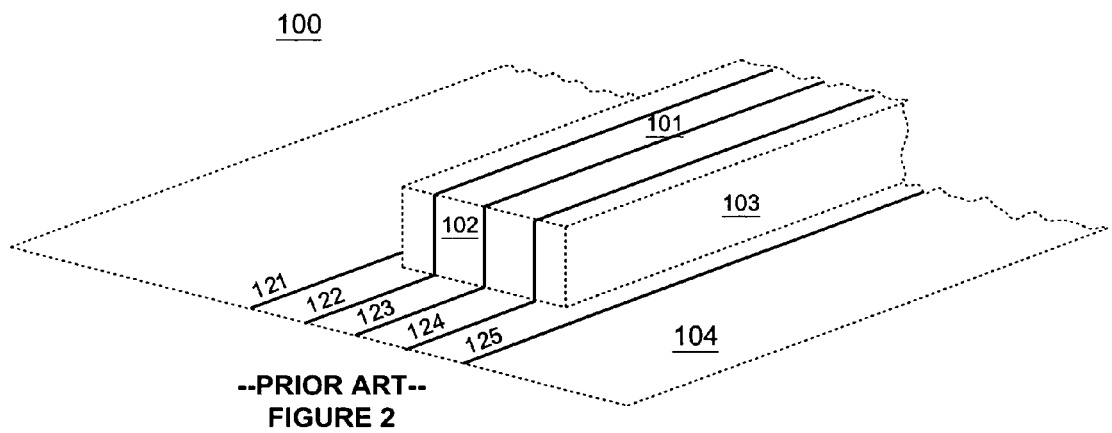
FIG. 2 illustrates an object being scanned by a plurality of lines in accordance with the prior art.
Figure 3:
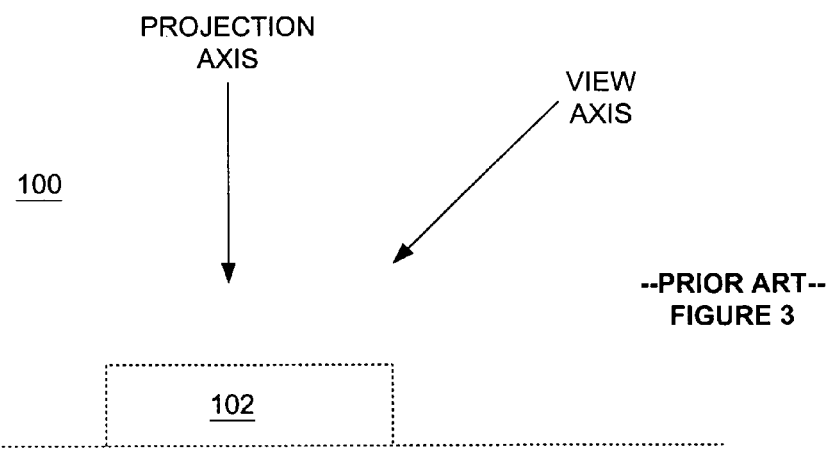
FIG. 3 illustrates a projection axis and a view axis associated with the lines of FIG. 2 in accordance with the prior art.

FIG. 12 illustrates a method in accordance with the present invention that will be discussed with reference to the system of FIG. 10 and the accompanying Figures. In order to better understand the methods discussed herein, terminology and characteristics unique to the present invention are described. The term "projection/view plane" refers to a plane formed by the projection axis and at least one point of the view axis. The term projection/view plane is best understood with reference to FIG. 3. Assuming that FIG. 3 represents a cross section of the object 100. The projection axis illustrated is directed such that it lies entirely within the plane formed by the sheet of paper including FIG. 3. Likewise, the view axis of FIG. 3 is also lying entirely within the plane represented by the sheet of paper of FIG. 3. In this example, the projection/view plane formed by the projection axis of FIG. 3 and at least one point of the view axis of FIG. 3 includes the sheet of paper on which the Figure is drawn.

Figure 4:
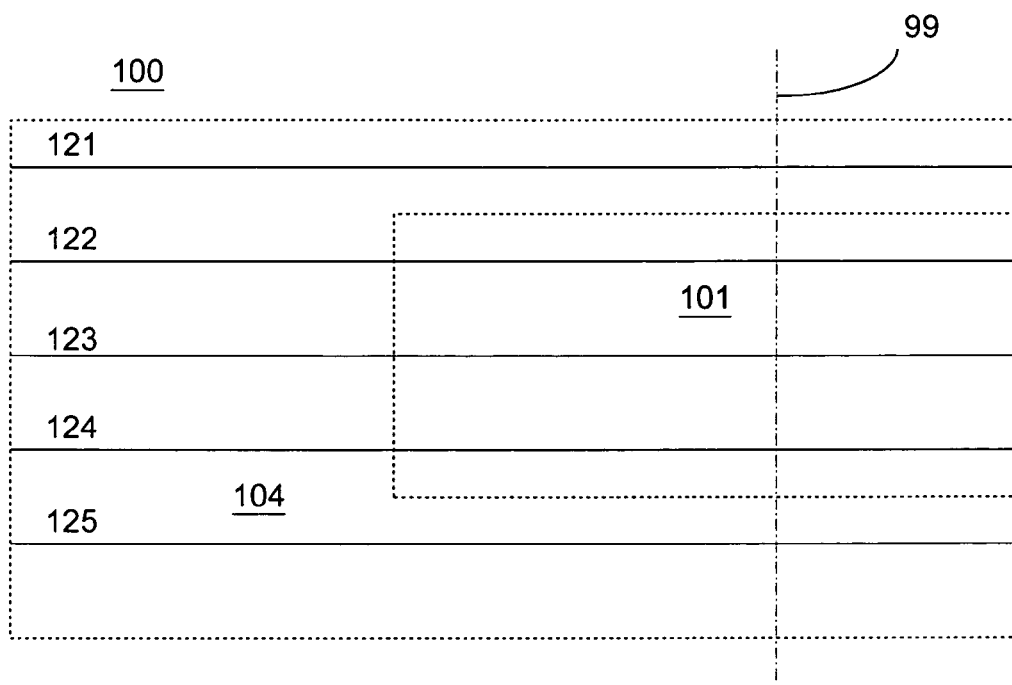
FIG. 4 illustrates the object of FIG. 1 from a point of reference equal to the projection axis of FIG. 3.
Figure 5:
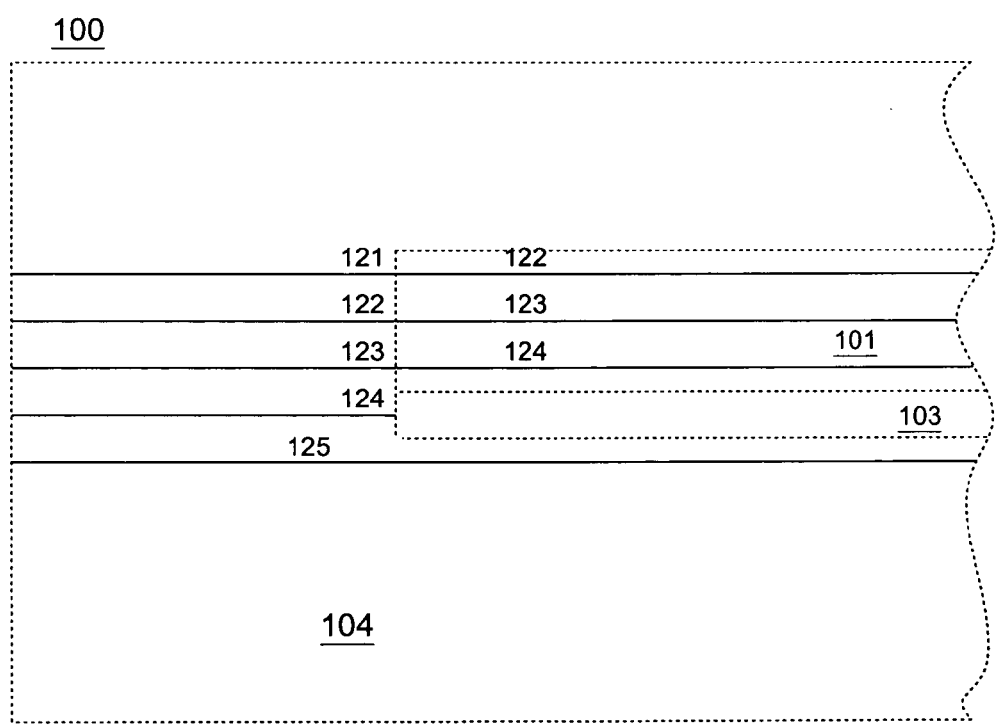
FIG. 5 illustrates the object of FIG. 3 from the view axis of FIG. 3.

However, if the view axis of FIG. 3 was actually oriented such that the endpoint near the viewing device is on the plane of the paper, while the arrow end of the view axis representation is pointing out of the paper towards the reader, it would not be possible to form a plane that includes the entire view axis and projection axis. Therefore, the projection/view plane can be described to contain substantially all of the projection axis and at least one point of the view axis, or all of the view axis and at least one point of the projection axis. For purposes of discussion herein, it will be assumed that the point of the view axis nearest the view device is the point to be included within that projection/view plane. For example, referring to prior art FIG. 4, the projection/view plane described with reference to FIG. 3 would be substantially orthogonal to the surface 104, and orthogonal to each of the lines 121–125. The projection/view plane is represented by line 99, which represents the plane from an edge view intersecting the lines 121–125.

At step 611 of FIG. 12, an image is projected having an encoding (variable) feature with a component, or components, that varies orthogonal to the projection/view plane. With respect to FIG. 13, the projection/view plane is illustrated by the line 936 indicating that the orientation of the view/projection plane is on edge such the plane appears to be a line, and each of the shapes or patterns 931–935 represent an encoding feature.

Each of the individual features 931–935 has a component (s) that varies in a direction orthogonal to the projection/view plane. For example, feature 933 varies orthogonal to the projection plane such that three individual lines can be identified. By varying the thicknesses of the three individual lines a unique pattern is associated with each of the features 931–935. For example, the bar code feature 933 varies orthogonal between no line, thin line, no line, thick line, no line, thin line, and no line. The individual lines of the feature 933 are projected parallel to the projection/view plane. Projecting lines parallel to the projection/view plane reduces, or eliminates, the viewed distortion affects of surface topology on the width of the lines. Therefore, because the viewed width of the individual lines making up the feature 933 do not distort substantially, the thickness, or relative thickness, of each individual line of the feature 933 can be readily identified independent of surface topology. As a result, the feature 933 can be identified substantially independent of surface topology.

Figure 13:
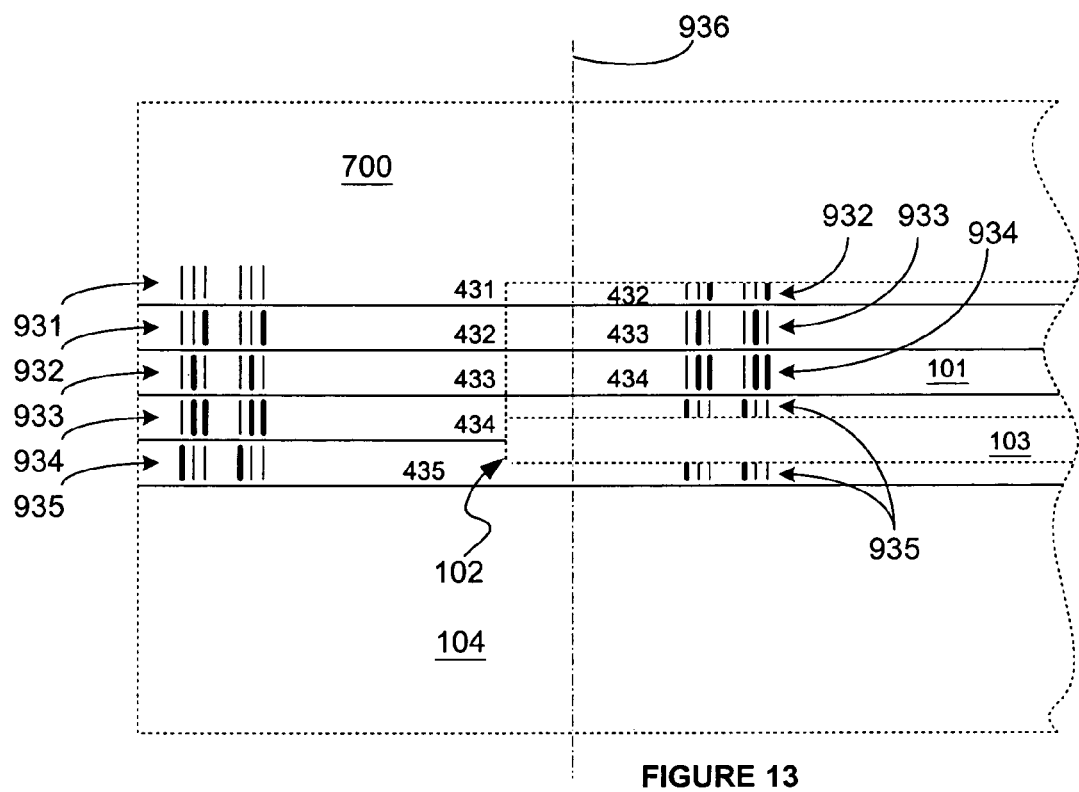
FIG. 13 illustrates, the object of FIG. 3 from a point of reference equal to the view axis of FIG. 3 in accordance with the present invention.

FIG. 13 displays a specific embodiment of an image having five separate lines (measuring features) 431–435. The lines 431–435 illustrated have lengths that run substantially orthogonal to the projection/view plane, and are uniformly spaced from each other in a direction parallel to the projection/view plane. By providing a plurality of lines which are detectable in the direction parallel to the projection/view plane, multiple measuring lines can be viewed and analyzed simultaneously. In addition to the lines 431–435, five unique bar codes 931–935 are also illustrated. Each of the unique bar codes (variable features) 931–935 are associated with, and repeated along a respective measuring feature 431–435. In other implementations, each bar code can be repeated along a measuring feature more than the two times illustrated. Note that the bar codes illustrated are illustrated as repeating sets. In other implementations, the bar codes would not need to be grouped in sets.

In a specific embodiment, the lines 431–435 and bar codes 931–935 are generated using visible light that is low-intensity, such that the pattern is eye-tolerant and skin tolerant. For example, the lines 431–435 can be viewed as white lines, and the bar codes 931–935 can be viewed as specific colors or combinations of colors. In another embodiment, high-intensity or laser light can also be used depending upon the application.

By associating bar codes to specific lines in the manner illustrated, it is possible to distinguish lines from one another even when they appear to be linearly coincident. For example, the lines 432 and 433 appear to be a continuous line at the edge of object 101. However, the lines 432 and 433 can be distinguished from each other by analyzing the (encoding feature) barcodes associated with each line. In other words, where line 432 and line 433 appear to the viewer to be a common line, it can now be readily determined that they are two different lines because the bar code associated with line 432 on the left would not be the same as the bar code associated with line 433 on the right.

In the specific example illustrated in FIG. 13, the analysis of the retrieved images would determine that there is a discontinuity somewhere between the left most bar code 932 and the right most bar code 933 causing the line segments 432 and 433 to appear as a common line. In a specific embodiment, the location of such an edge can be determined with greater precision by providing repeating bar code patterns in relatively close proximity to one another. For example, the edge where surface 102 meets surface 101 can be determined only to an accuracy equal to the spacing between adjacent bar codes. This is because when the analysis encounters what appears to be a single line having two different bar codes it is unknown where between the two bar codes the discontinuity has occurred. Therefore, by repeating the bar code more frequently along the measuring lines of FIG. 13 the location of discontinuities can be more accurately identified.

The encoding features 931–935 of FIG. 13 are non-repeating in that no two bar codes are the same. However, an encoding value, or sequence, can be repeated within a projected image as long as ambiguity is avoided. For example, if the image includes 60 lines (measuring features) using a binary encoding, 6 bits of data are needed to identify each line uniquely. However, due to the fact that the range of focus of the scanner is limited by the depth of field, each individual line of the 60 lines can show up as a recognizable image only within a certain range.

Figure 25:
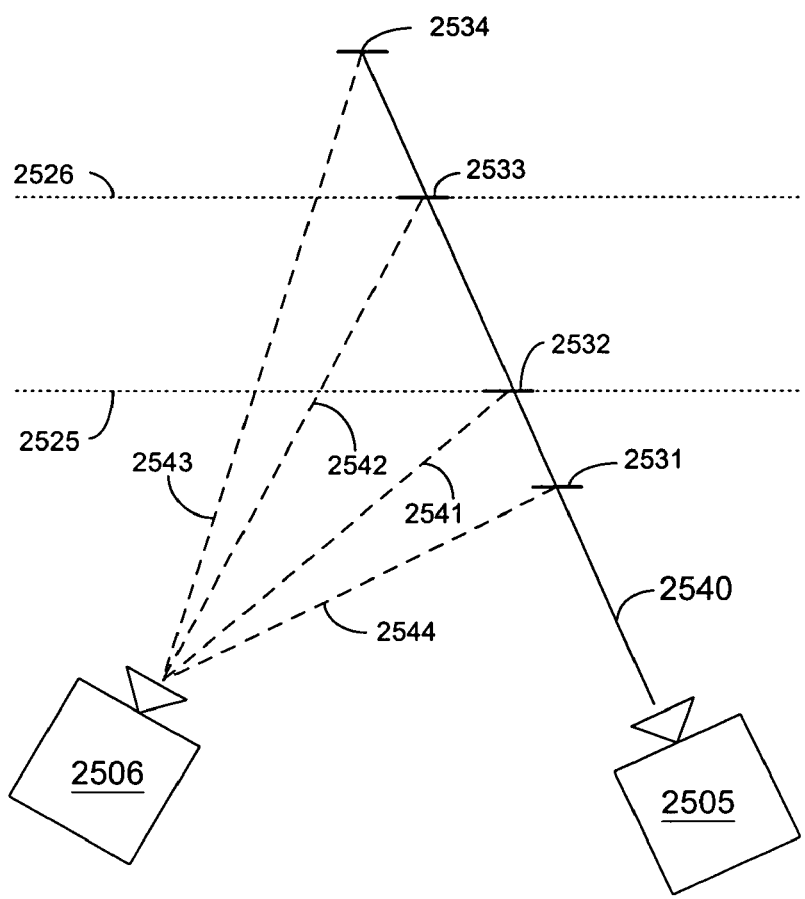
FIG. 25 illustrates a projected image feature being reflected off surfaces at different depths in accordance with the present invention.
Figure 26:
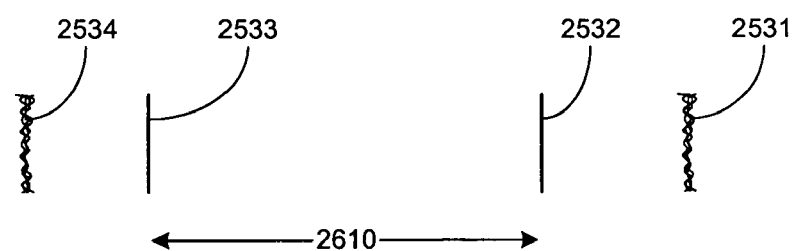
FIG. 26 illustrates the projected image of FIG. 25 as viewed at the different depths.

FIGS. 25 and 26 better illustrate how the depth of field affects the repeating of features. FIG. 25 illustrates a projector projecting a SHAPE along a path 2540. When the SHAPE is projected onto a surface its image is reflected along a reflection path to a viewing device 2506. For example, reflection path 2544 results when the SHAPE is reflected off a surface at the location 2531, a reflection path 2541 results when the SHAPE is reflected off a surface at the location 2532, a reflection path 2542 results when the SHAPE is reflected off a surface at the location 2533, and a reflection path 2543 results when the SHAPE is reflected off a surface at the location 2534.

FIG. 26 represents the SHAPE as the viewer 2506 would view it. Specifically, the image reflected off of the surface 2531, which is the surface closest to the projector, is viewed as the right most image in FIG. 26, while the image reflected off of the surface 2534, which is the surface furthest from the projector, is viewed as the left most image in FIG. 26. However, it should be noted, that the left and right most images, which are furthest and closest to the projector 2505 respectively, are out of focus. Because they are out of focus they can not be accurately detected based upon the image received by the viewing device 2506.

Figure 6:
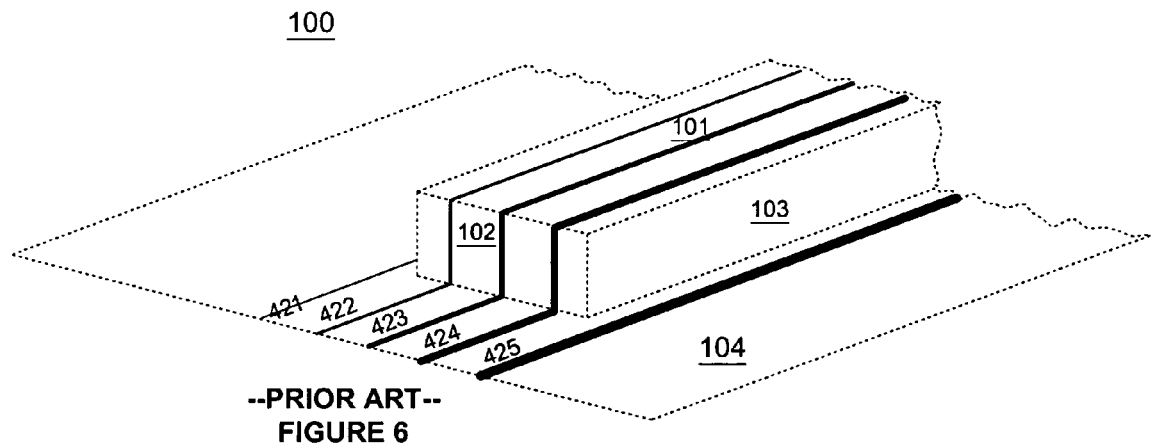
FIG. 6 illustrates an object having a plurality of lines of varying thickness projected upon it in accordance with the prior art.
Figure 7:
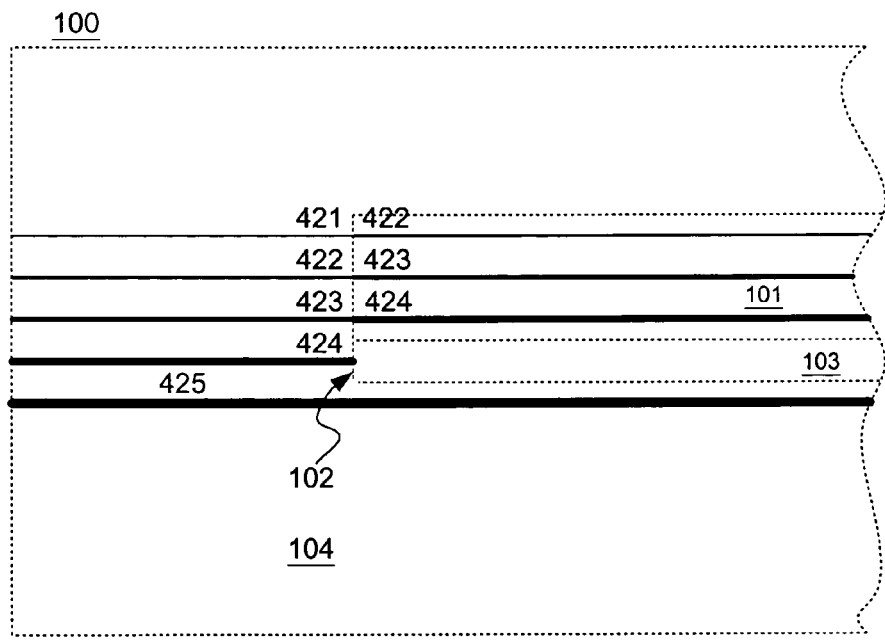
FIG. 7 illustrates the object of FIG. 6 from a point of reference equal to the view axis as shown in FIG. 3.

Referring back to FIG. 25, any surface closer to the projection device 2505 than plane 2525, or further from the projection device 2505 than the plane 2526 is not capable of reflecting a usable SHAPE because it is outside the viewable range 2610, or field of view. Therefore, the SHAPE can be repeated and still be uniquely identified, so long as the repeated SHAPE can not be viewed within the range 2610 of FIG. 6.

In a specific embodiment, a projector projects approximately 80 lines. Each of the 80 lines has a color-coded encoding sequence. For example, if three colors are used (red, blue, green), an encoding feature having three color locations could uniquely identify 27 different lines. This coding sequence of 27 lines can be repeated three times to cover all 80 lines, provided the field of view is such that lines having the same encoding can not be viewed at the same location. In another embodiment, five color locations can be added with or without increasing the number of lines in a sequence to provide recognition capability where a specific color location may be lost.

This means that coding features may be repeated, as long as the fields of view in which each of the repeating features may be viewed do not overlap. Thus, a sequence of 12 unique encoding features, requiring only four bits of binary data, can be repeated five times to encode all 60 lines, provided there is no chance for features to be viewed at the same location.

By providing a pattern having a large number of measuring features with associated coding features reference independent scanning is achieved. Specifically, neither the object nor the scanner need to be fixed in space, nor with reference to each other. Instead, on a frame by frame basis, the reference independent scanner retrieves enough measuring information (a 3D cloud), which is accurate due to the encoding feature, to permit registration to its adjacent frame. Registration is the processes which determines the overlapping features on adjacent frames to form an integrated map of the object.

Figure 14:
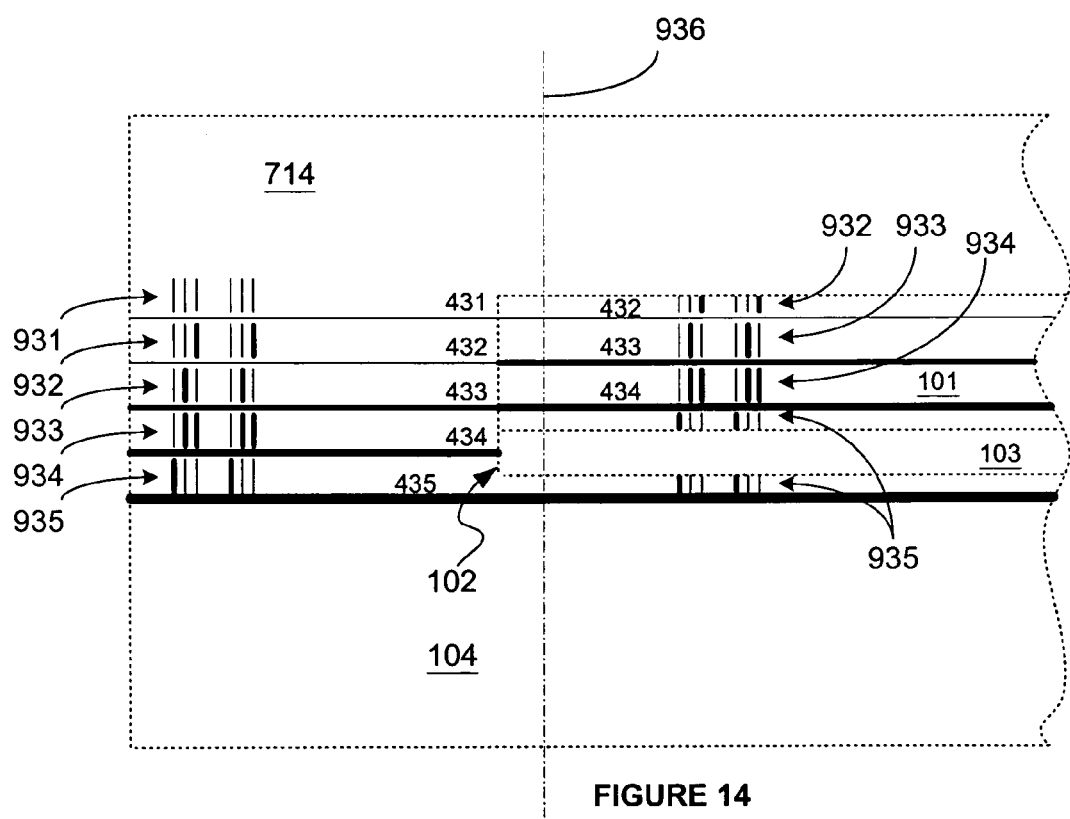
FIG. 14 illustrates, the object of FIG. 3 from a point of reference equal to the view axis of FIG. 3 in accordance with the present invention.

FIG. 14 illustrates the object of FIG. 13 whereby the measuring lines 431–435 have varying thickness. However, the thickness of lines 431–435 is subject to distortion. Thereby making identification of the individual lines 431–435 based upon their thickness alone prone to error. This is better illustrated with reference to FIG. 15.

Figure 8:
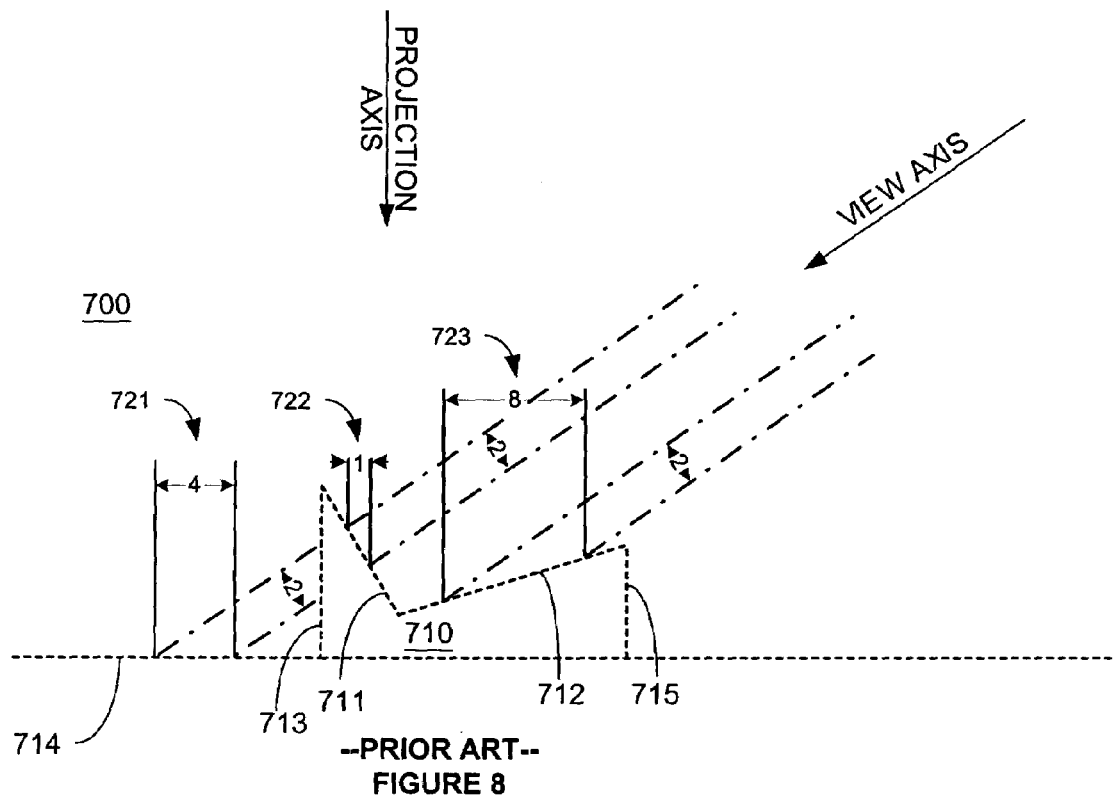
FIG. 8 illustrates an object from a side view having varying projected line thickness in accordance with the prior art.
Figure 9:
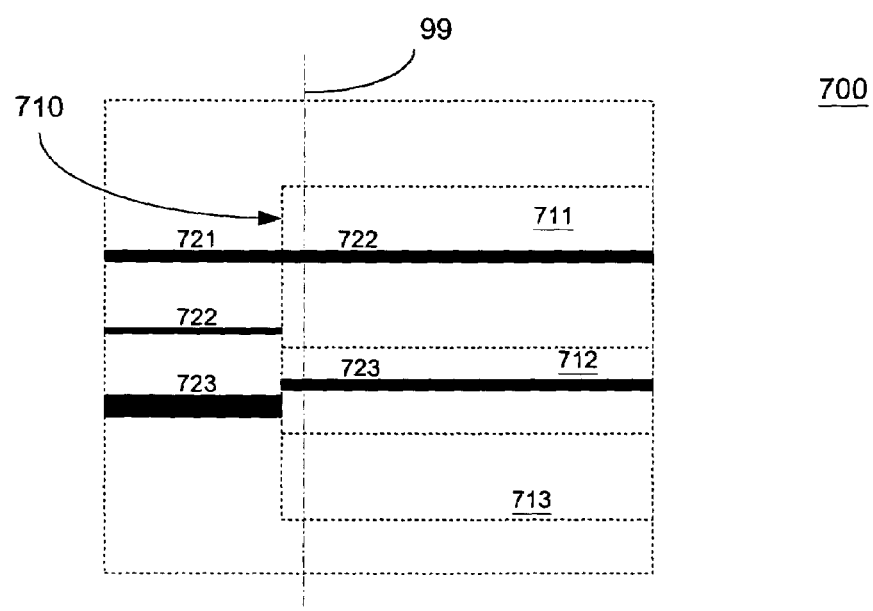
FIG. 9 illustrates the object of FIG. 8 from point of reference equal to the view axis of FIG. 8.
Figure 15:
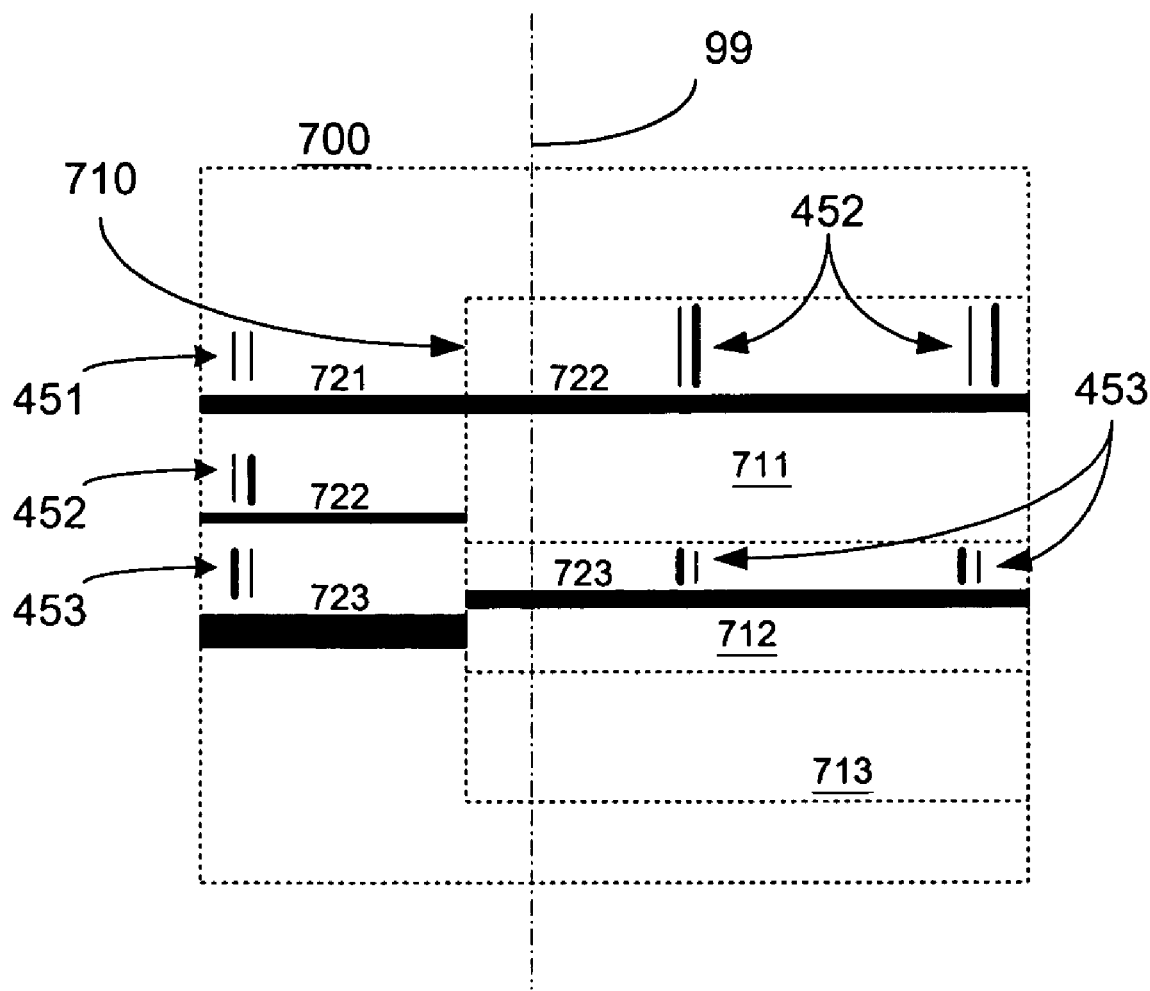
FIG. 15 illustrates an object having a pattern projected upon it in accordance with the present invention.

FIG. 15 represents the object 700 of FIGS. 8 and 9 having a pattern in accordance with the present invention projected upon its surface. FIG. 15 illustrates the projection of lines 721–723 having varying widths. As previously discussed, the lines 722 and 723, when projected onto the surfaces 711 and 712 respectively, appear to have the same line thickness as line 721. Therefore, merely having measuring lines of varying thickness will not allow an analysis of the images to determine which line is which. However, by further incorporating the encoding features 451–453, such that they have a component that varies orthogonal to the projection/view plane, identification of the lines 721–723, and the subsequent mapping analysis, is improved over the prior art.

One skilled in the art will recognize that the specific implementations illustrated, whereby an encoding feature is projected to have a portion perpendicular to a projection/view plane, is advantageous over the prior art in that it allows for analysis of the received images to more accurately identify specific lines associated with the pattern. One skilled in the art will further recognize and understand that the specific implementation described herein has been described with reference to lines and bar codes. However, other patterns, shapes and features can also be used.

Referring to FIG. 16, a table is illustrated where a specific set of shapes used in a direction orthogonal to the projection/view plane are illustrated. Column 1 of table 16 represents unique feature identifiers. The columns 2–4 of table 16 illustrate specific manners in which each feature identifier can be represented. Column 2 indicates bar codes. Column 3 indicates colors capable of being used either alone or with other encoding features. Note that some types of encoding features, including color features, can be implemented as an integral part of a measuring feature as well as an encoding feature separate from the measuring feature. Likewise, other types of encoding can be based upon the intensity at which a measuring feature and/or its encoding feature is projected. Column 4 represents patterns that can be utilized either independently from the shape to identify the shape, or in combination as part of a shape. In other words, a line comprising a repeating pattern sequence of the type illustrated in Column 4 can be provided. In this manner, the change of pattern in a direction orthogonal to the projection/view plane can be relative to the actual shape itself. In addition, one of ordinary skill in the art will recognize that many variations as to variable components would be anticipated by the sent invention.

FIG. 17 illustrates in tabular form, the use of unique non-repeating identifiers for each line. For example, referring to the first row of FIG. 17 the sequence 0-F sequentially is presented. In one implementation, each of the values from 0 through F will represent a unique code associated with a specific line. One skilled in the art will recognize that in order to identify the specific codes, some type of spacer may need to exist between each individual code. For example, a long space, or a unique code can be used.

In a system used to project and analyze four lines, each with one of the sequences illustrated in FIG. 17, it would be possible to identify which one of the four lines is being analyzed once a sequence of three codes has been retrieved. Generally, because the codes vary orthogonal to the projection/view plane missing codes may not pose a problem of misidentification.

FIG. 18 illustrates four unique repeating code sequences. The letter S in table 18 is utilized to represent a spacer used between repeating sequences. A spacer can be some unique identifier specifying where each of the repeating codes of the encoding sequence begins and/or ends.

Returning to the flow of FIG. 12, once the image has been projected having an encoding feature orthogonal the projection/view plane, a representation of the surface image is received at a viewer. This is analogous to the discussion of FIG. 10 whereby the viewer 970 receives the reflected image. Next, at step 613, the location of a point associated with an object is determined based upon the orthogonally varying feature. In a specific embodiment of the present invention, the point is based upon the variable component because each one of the shapes, e.g. lines is qualified to a unique code pattern prior to being used for object analysis.

FIG. 19 illustrates sub steps to be associated with step 611 of FIG. 12. At step 621, a first image is projected, while at step 622 a second feature is projected. Referring to FIG. 14, the first image can be analogous to the combination of the measuring line 431 and its associated encoding features 931. In the similar manner, the second feature could be represented by the combination of the measuring line 432 and its encoding features 932. Note that in addition to being able to analyze line 431 with respect to the features 931, it would also be possible in another embodiment to determine the identity of line 431 based upon the encoding features 932. In other words, a specific line in a group of lines, such as illustrated in FIG. 14, can be identified based on more than one of the various encoding features. However, in a specific embodiment, only the adjacent set of encoding features, or adjacent sets of encoding features, would be utilized. In addition, steps 621 and 622 can occur at different times as discussed with reference to FIG. 23.

Figure 21:
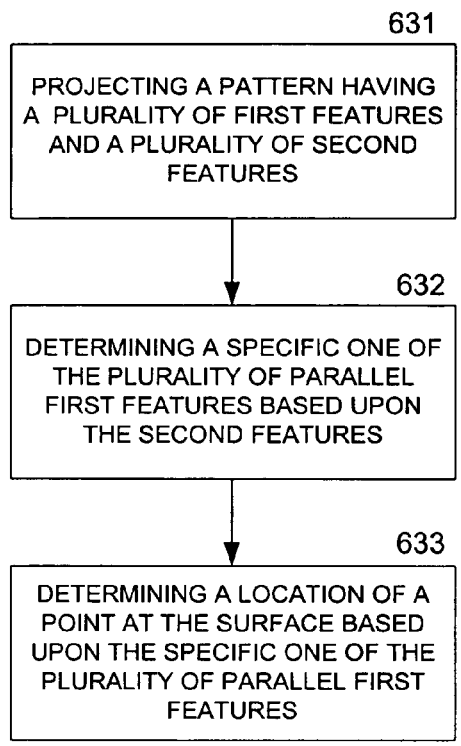

FIG. 21 illustrates another method in accordance with the present invention. At step 631, a plurality of first features, and a plurality of second features are projected. These features may be projected simultaneously, or at separate locations.

At step 632, one of the plurality of first features is determined, or identified, based upon the second features. Referring to FIG. 14, the plurality of first features would include the lines measuring 431–435. By utilizing the second features, the bar code 931–935, a specific one of the lines 431–435 can be identified.

At step 633, the location of a point at the surface is determined based upon the specific one of the plurality of parallel first features.

This specific embodiment is an advantage over the prior art, in that a line identified by the analysis of the received shape is not utilized until its identity is verified based upon the encoding information.

Figure 22:
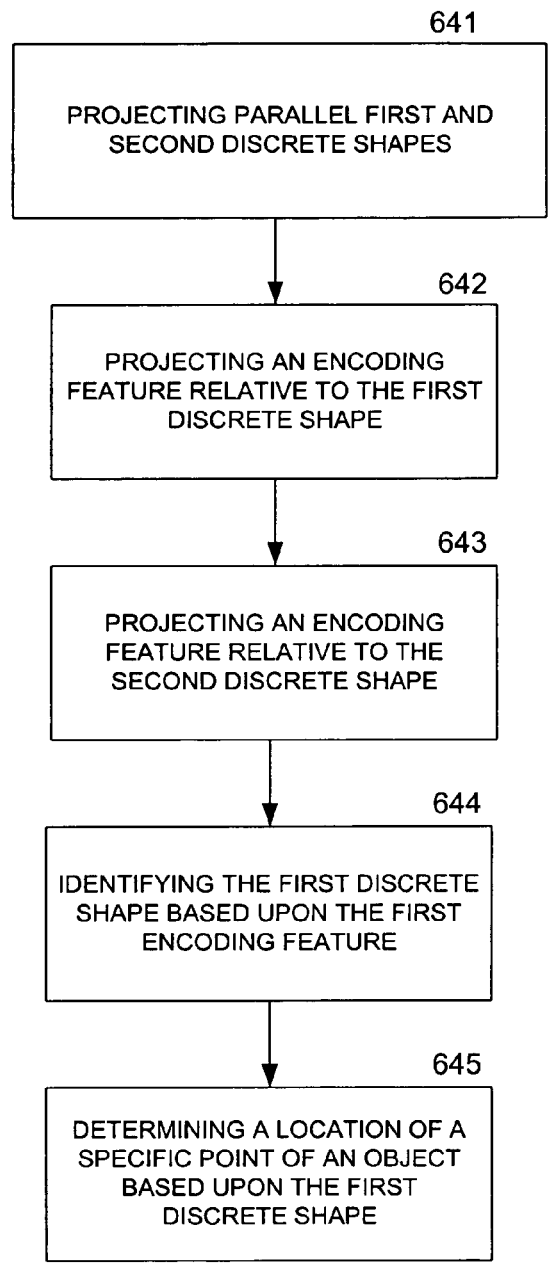

FIG. 22 illustrates another method in accordance with the present invention. At step 641 parallel first and second discrete shapes are projected. Examples of such discrete shapes would include the lines 431 and 432 of FIG. 14. However, one of ordinary skill in the art will recognize that a variety of other parallel shapes could be projected.

At step 642, an encoding feature relative to the first discrete shape is projected. Again, referring to FIG. 14, the encoding feature relative to the line 432 could include the encoding feature 932 or even an encoding feature 933.

At step 643, an encoding feature relative to the second discrete shape is projected.

At step 644 the first discrete shape is identified based upon the first encoding feature. This is accomplished in a manner similar to as discussed previously.

At step 645 a location of a specific point of an object is determined based upon the first discrete shape.

Figure 23:
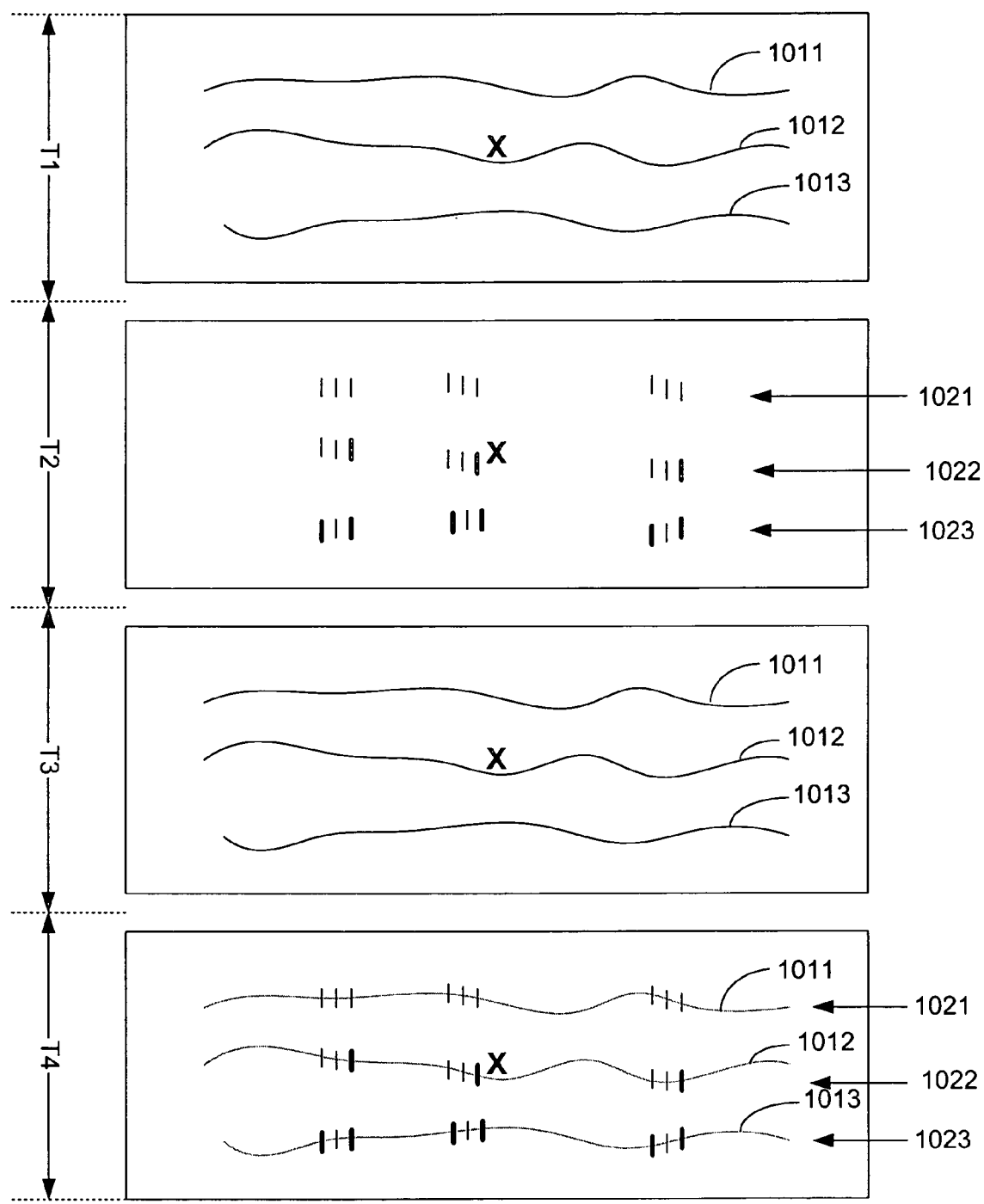
FIG. 23 illustrates a sequence of images to be projected upon an object in accordance with an embodiment of the present invention.

FIG. 23 illustrates another embodiment of the present invention. Specifically, FIG. 23 illustrates a series of images projected at times T1, T2, T3 and T4. At time T1, the image projected includes measuring features 1011 through 1013. During time T1, no encoding feature is projected. During time T2, an image containing encoding features 1021–1023 is projected. The patterns of times T1 and T2 are repeated during times T3 and T4 respectively. The result of alternating the projection of encoding and measuring features is that denser patterns can be used, allowing for more information to be obtained. Note that the image of time T4 shows the encoding features 1021–1023 overlying the measuring features 1011–1013. However, in one embodiment, the measuring features have been included for illustration purposes only, and would not generally be present at the same time as the encoding features.

In yet another embodiment of the present invention, FIG. 24 illustrates an image having features with different characteristics. Specifically, FIG. 24 illustrates an image 1100 having lines 1131 through 1134 with a distance X between the individual lines, while the distance between lines 1134, 1135, and 1136 have a substantially greater distance Y separating the lines. By allowing for features having different isolation characteristics, it is possible to provide for a high-resolution feature. In other words, the line 1135 can be used to map surface features that otherwise may not be mappable. Note that the pattern 1100 could be used with or without the coding techniques described herein.

Once a scanner receives, or views, a projected frame pattern, the frame pattern is digitized into a plurality of 2D points (2D image frame). Because the projection and view axis of the scanner are fixed and known, each 2D point of the 2D image frame can be converted into a 3D point using conventional 3D imaging techniques, provided each 2D point of the 2D image frame can be correlated to a projected point. The use of a projected frame pattern that has encoding features enables correlation of the points of the 2D image to a respective projected point.

Multi-frame reference independent scanning is described herein in accordance with another aspect of the present disclosure. In a specific embodiment, multiple 3D image frames are received by using a hand-held scanner to scan an object one frame at a time to obtain a plurality of frames, where each frame captures only a portion of the object. With reference to multiple frames, reference independent scanning has a spatial position that is frame-by-frame variable relative to the object being scanned, and whose spatial position is not fixed, or tracked, relative to a reference point. For example, there is no fixed reference point relative to the object being scanned.

One type of reference independent scanner disclosed herein includes a hand-held scanner that projects a pattern in successive frames having measuring features and encoding features. This allows each viewed point of a frame to have a known corresponding projected point, thereby enabling the 2D frame data to be converted into 3D frame data.

Figure 27:
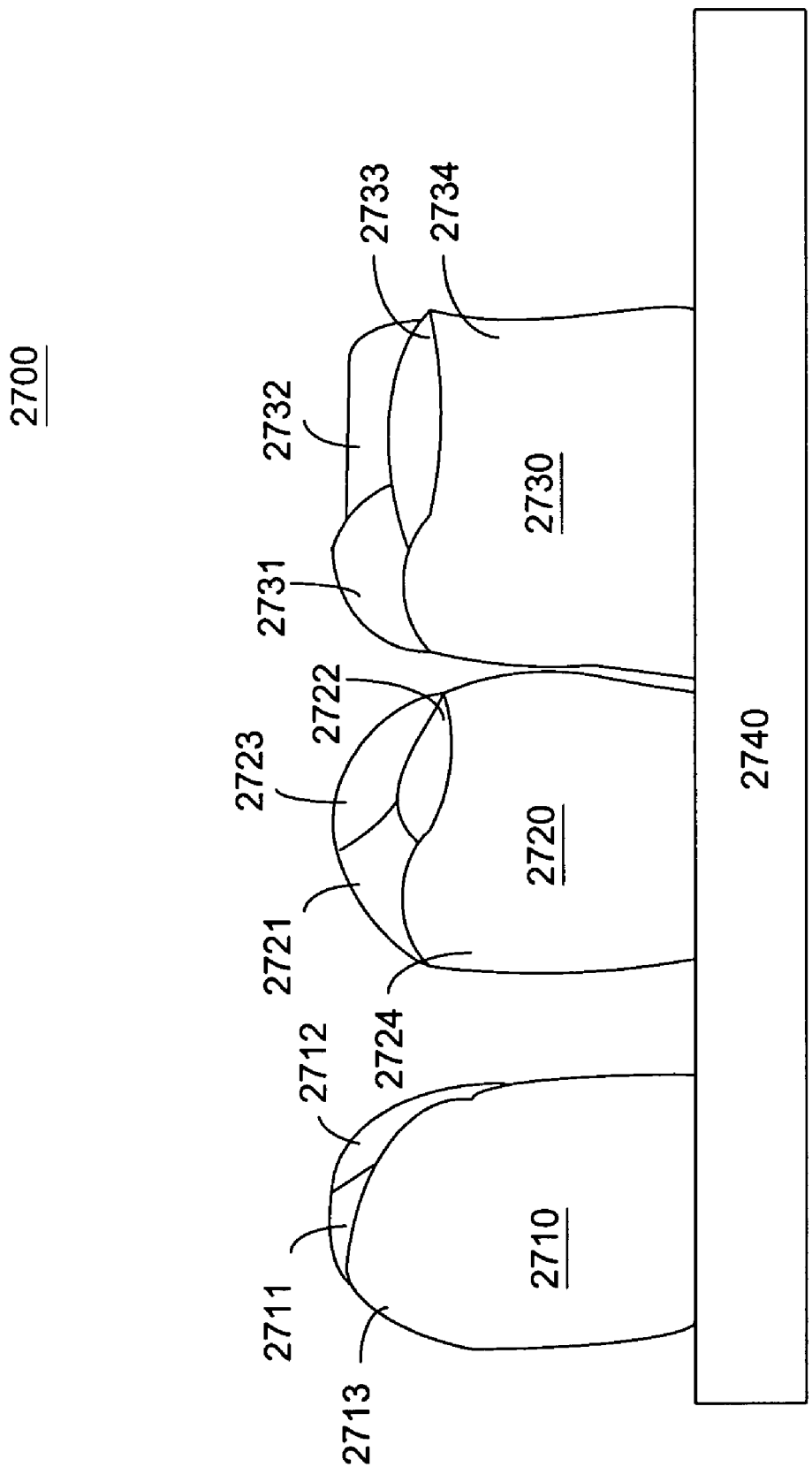
FIGS. 27–30 illustrate a dentition object from various perspectives in accordance with the present invention.
Figure 28:
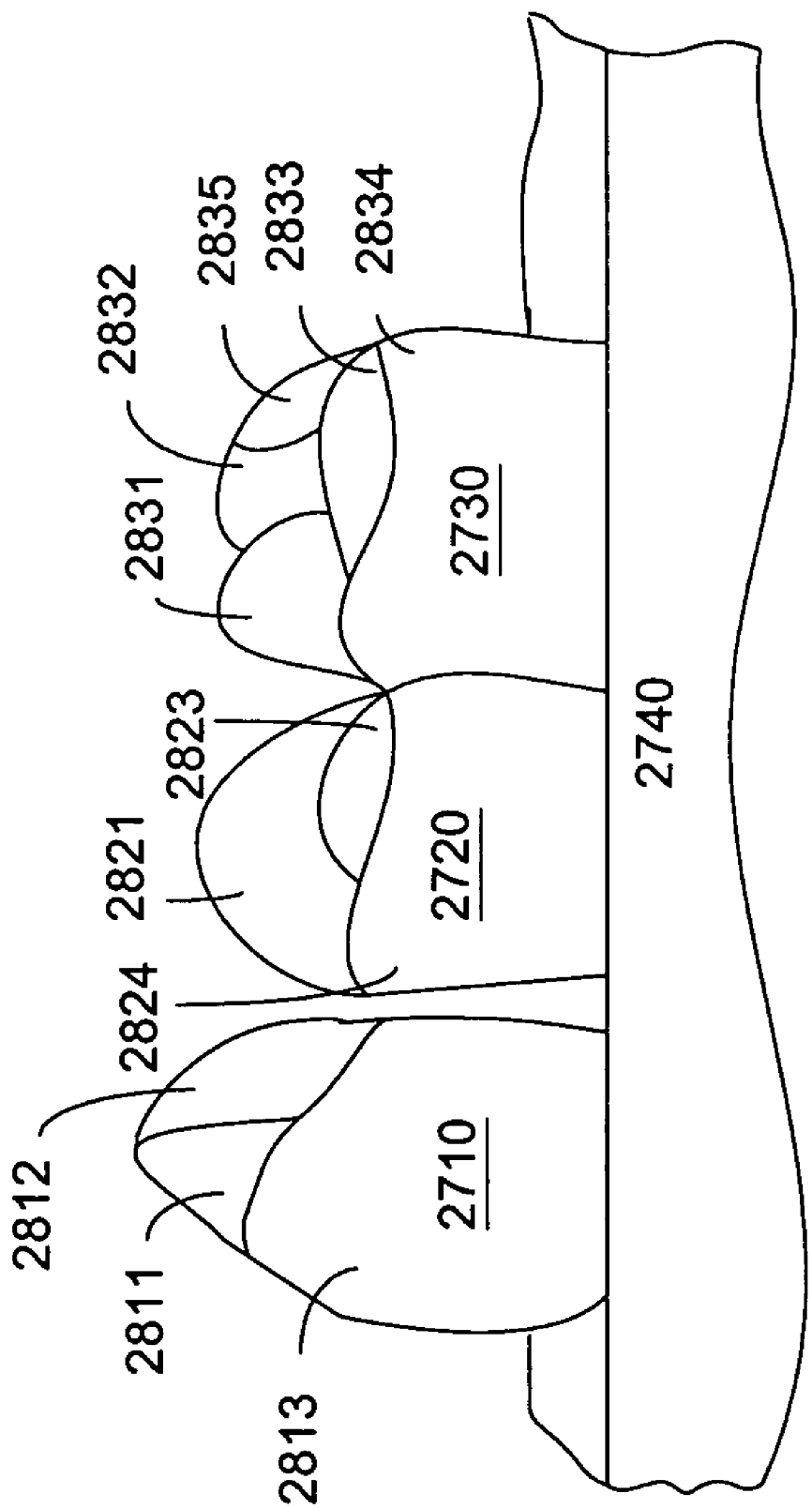

FIGS. 27–28 are used to discuss multiple frame reference independent scanning.

Figure 30:
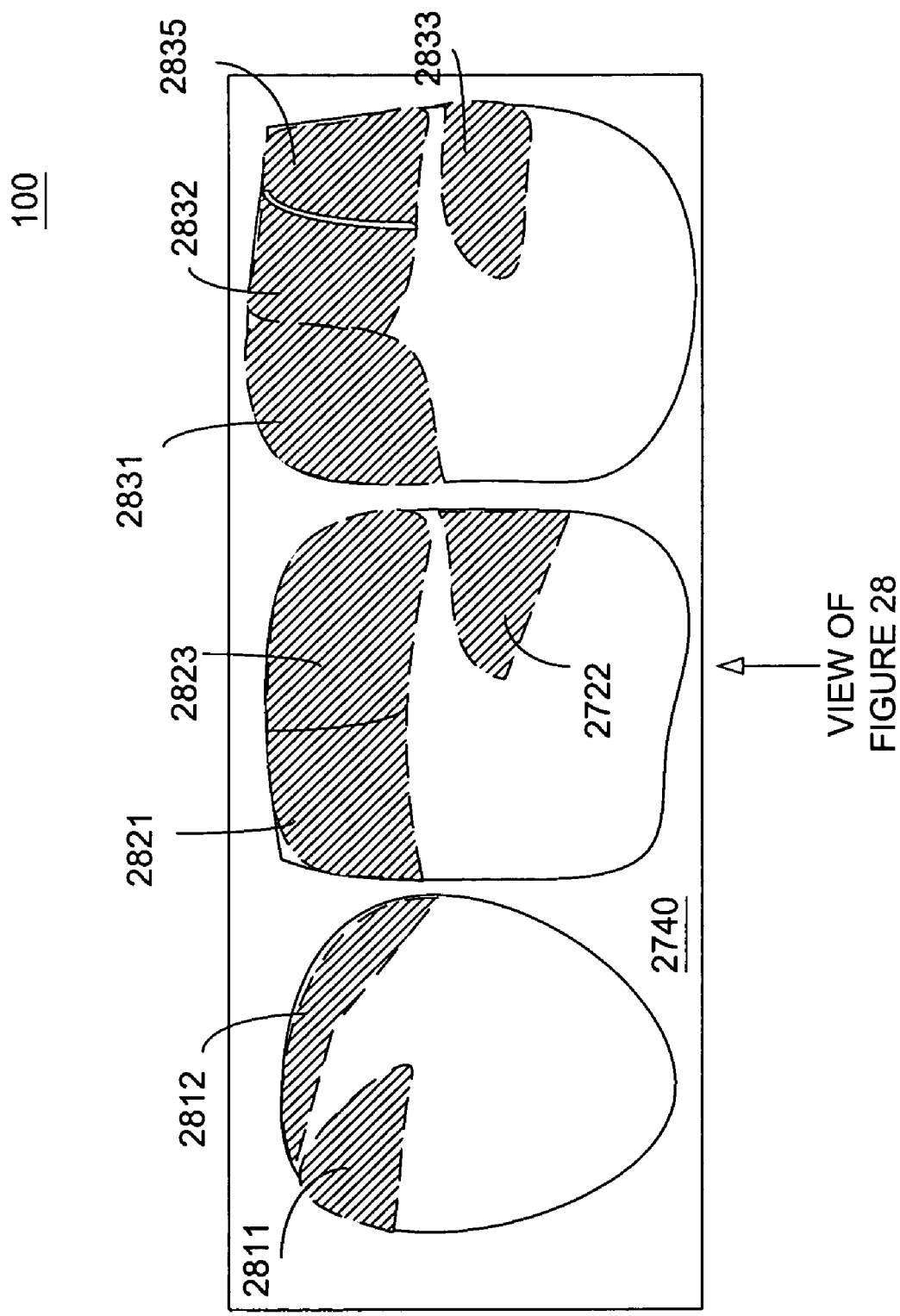

FIGS. 27, 28, and 30 illustrate an object 2700 from different points of view. As illustrated in FIG. 27, the object 2700 includes three teeth 2710, 2720, and 2730, and a gum portion 2740 that is adjacent to the three teeth.

The FIG. 27 point-of-view is such that a plurality of non continuous surface portions are viewed. For example, from the FIG. 27 point-of-view three noncontiguous surface portions 2711–2713 are viewed. The surface portion 2713 represents a side portion of the tooth 2710. The surface portion 2711 represents a portion of the tooth 2710 biting surface that is not continuous with surface portion 2713. The surface portion 2712 represents another portion of the tooth 2710 biting surface that is not continuous with either portion 2711 or 2713. In a similar manner, tooth 2720 has four surface portions 2721–2724, and tooth 2730 has four surface portions 2731–2734.

FIG. 28 illustrates the object 2700 from a slightly different point-of-view (FIG. 28 point-of-view). The point-of-view change from FIG. 27 to FIG. 28 is the result of the viewer, i.e. scanner, moving in a direction that allows a greater portion of the upper teeth surfaces to be viewed. The change in point-of-view has resulted in variations to a plurality of viewed surface portions. With respect tooth 2710, tooth portion 2813 now represents a smaller 2D surface than did its corresponding tooth portion 2713; while tooth portions 2811 and 2812 now are viewed as larger 2D surfaces than their corresponding portions 2711 and 2712 of FIG. 27.

With respect to tooth 2720, surface 2824 now is viewed as a smaller 2D surface than its corresponding tooth surface 2724 of FIG. 27. With respect to tooth 2720; tooth surface 2821 represents a continuously viewed tooth surface that includes both of the surfaces 2721 and 2723 from the FIG. 27 point-of-view.

With respect to tooth 2730, the viewed 2D surfaces 2832 and 2835 each include portions of surface 2732 and previously unviewed surface area.

This is the result of a topographical feature of the tooth 2730, which resulted in the inability of the surface 2732 to be viewed continuously from the second frame point-of-view.

Figure 29:
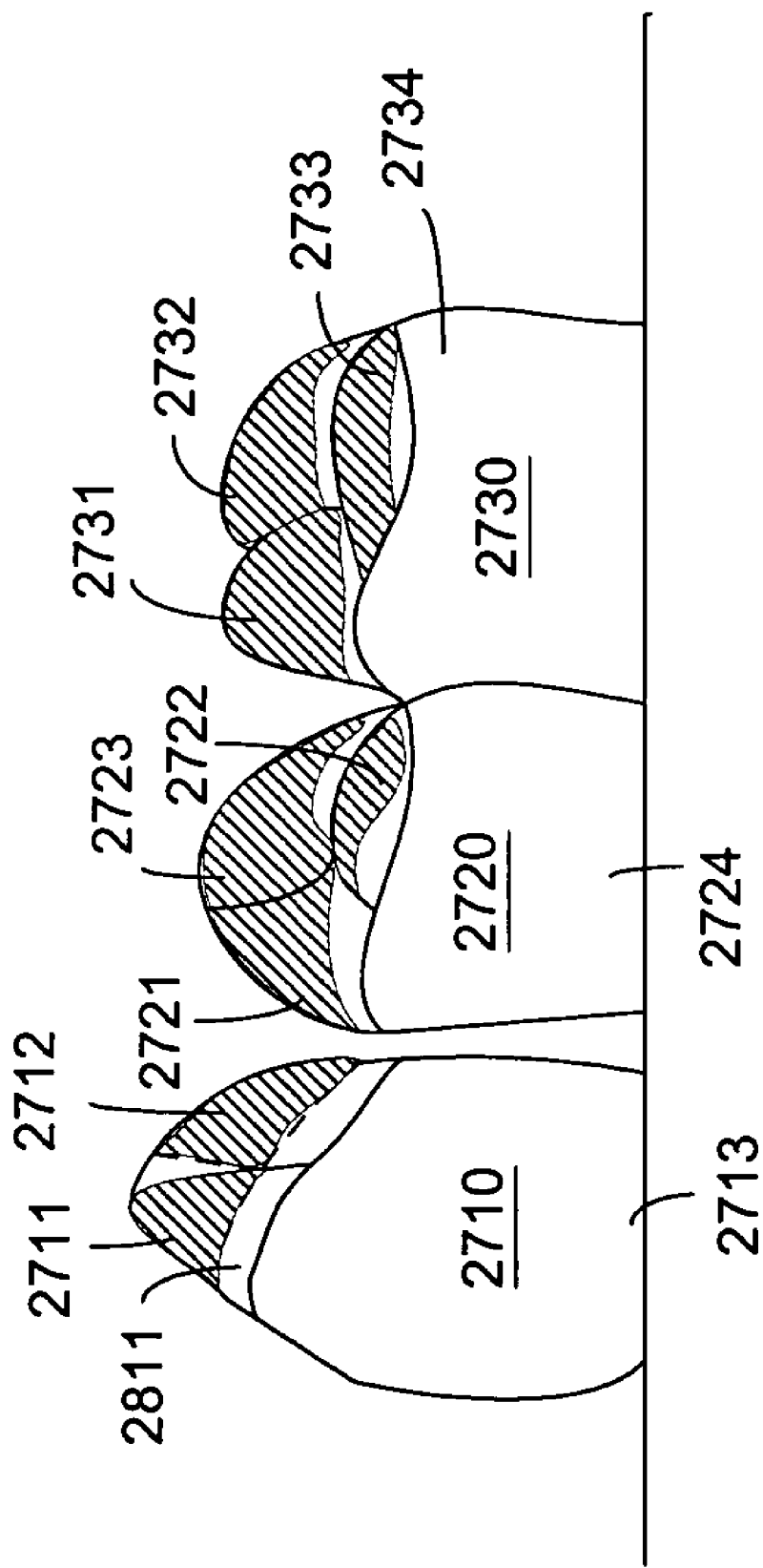

The relationship of the tooth portions of FIG. 27 to the tooth portions of FIG. 28 are better understood with reference to FIG. 29. Specifically, FIG. 29 is from the same point-of-view as FIG. 28 with the viewed surface portions of FIG. 27 indicated as shaded areas. For example, surface portion 2711 of FIG. 27 is represented as a shaded portion within the surface portion 2811. As illustrated, the change in the point-of-view between FIG. 27 and FIG. 28 results in a viewed surface portion 2811 that encompasses the smaller viewed surface portion 2711. Likewise, the change in perspective has resulted in different surface portions being viewed.

FIG. 30 illustrates the object 2700 from another point-of-view. Specifically, the FIG. 30 point-of-view is from directly over the teeth 2710–2730. Superimposed onto FIG. 30 are the viewed surface portions of FIG. 28. The object 2700 illustrated in FIGS. 27–30 will be referenced further herein to describe a specific embodiment of multiframe reference independent scanning.

Figure 31:
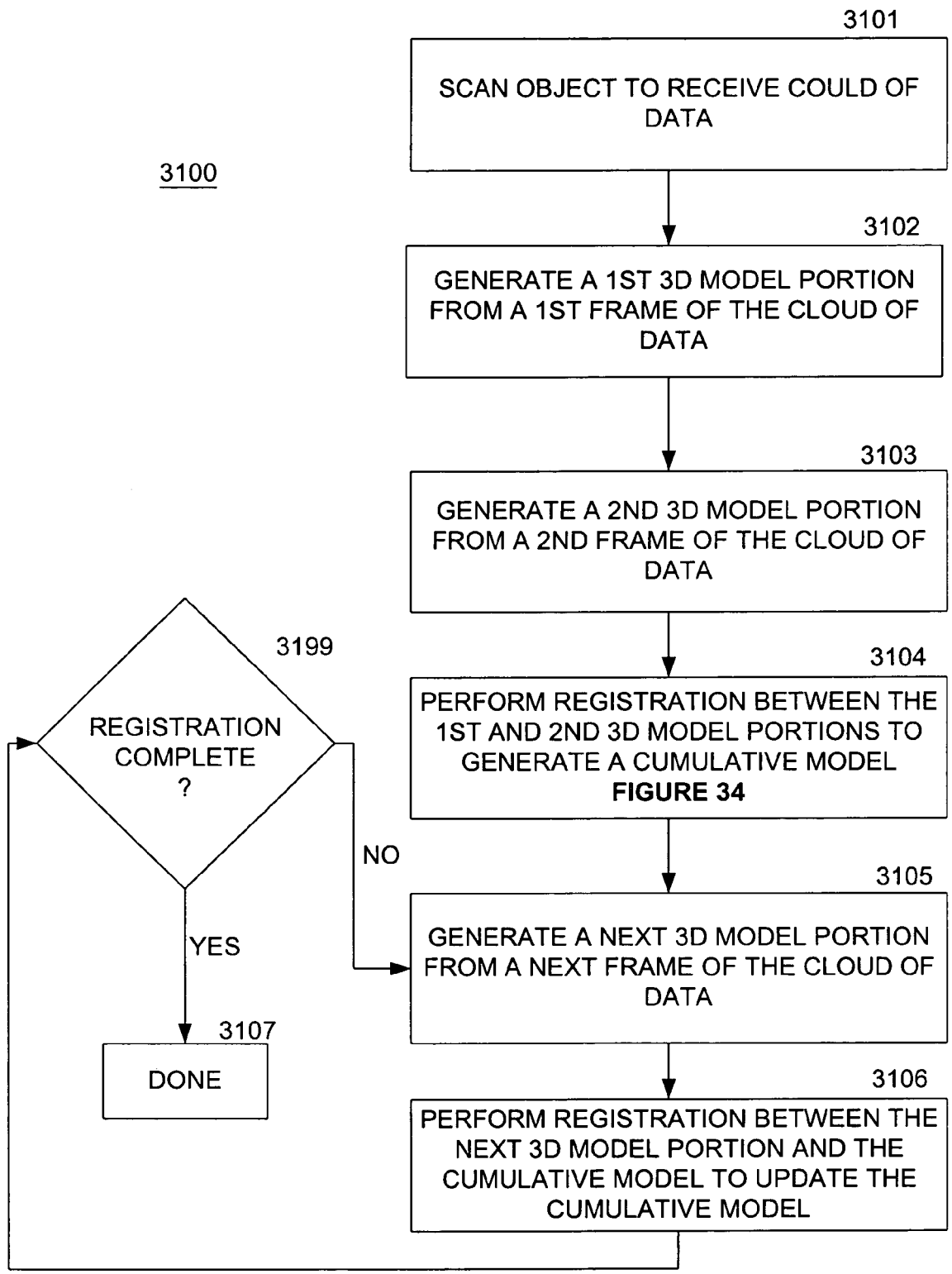
FIG. 31 illustrates a method in accordance with a specific embodiment of the present invention.

FIG. 31 illustrates a method 3100 in accordance with a specific embodiment of reference independent scanning. At step 3101 the object is scanned to obtain a 2D cloud of data. The 2D cloud of data includes a plurality of frames. Each of the frames has a plurality of 2D points, which, if viewed, would represent a 2D image.

At step 3102, a first frame of the 2D cloud of data is converted to 3D frame model. In one embodiment, a 3D frame model is a 3D point model, which includes a plurality of points in three-dimensional space. The actual conversion to a 3D frame point model is performed on some or all of the frame's 2D cloud of data using conventional techniques for converting a scanned 2D cloud of data into a 3D point model. In a specific embodiment using encoding features, as disclosed herein, surfaces with non continuous viewed surfaces, such as the teeth 2710–2730 of FIG. 27, can be successfully scanned frame-by-frame.

Figure 32:
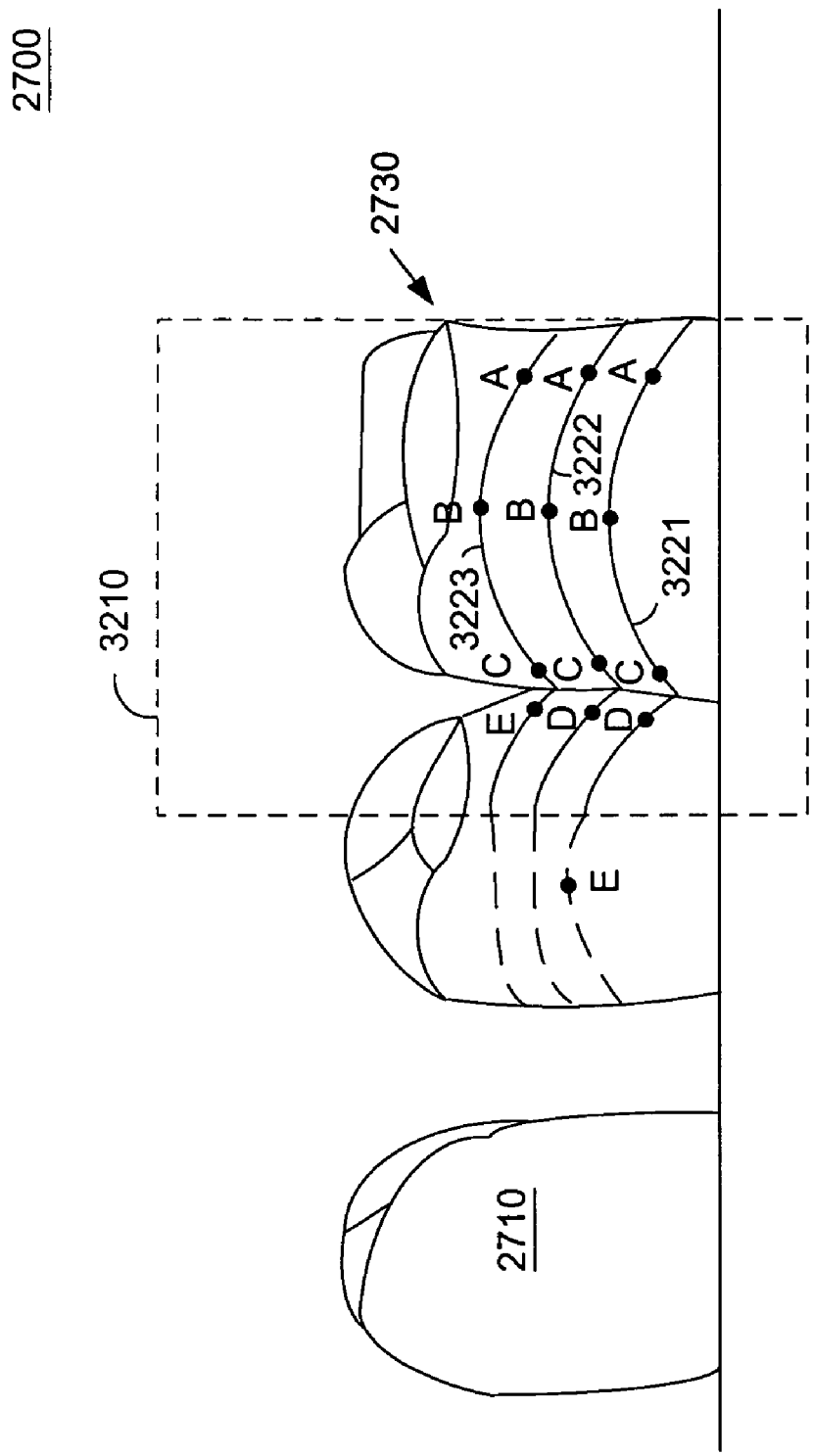
FIGS. 32 and 33 illustrate a dentition object being scanned from various perspectives in accordance with the present invention.
Figure 33:
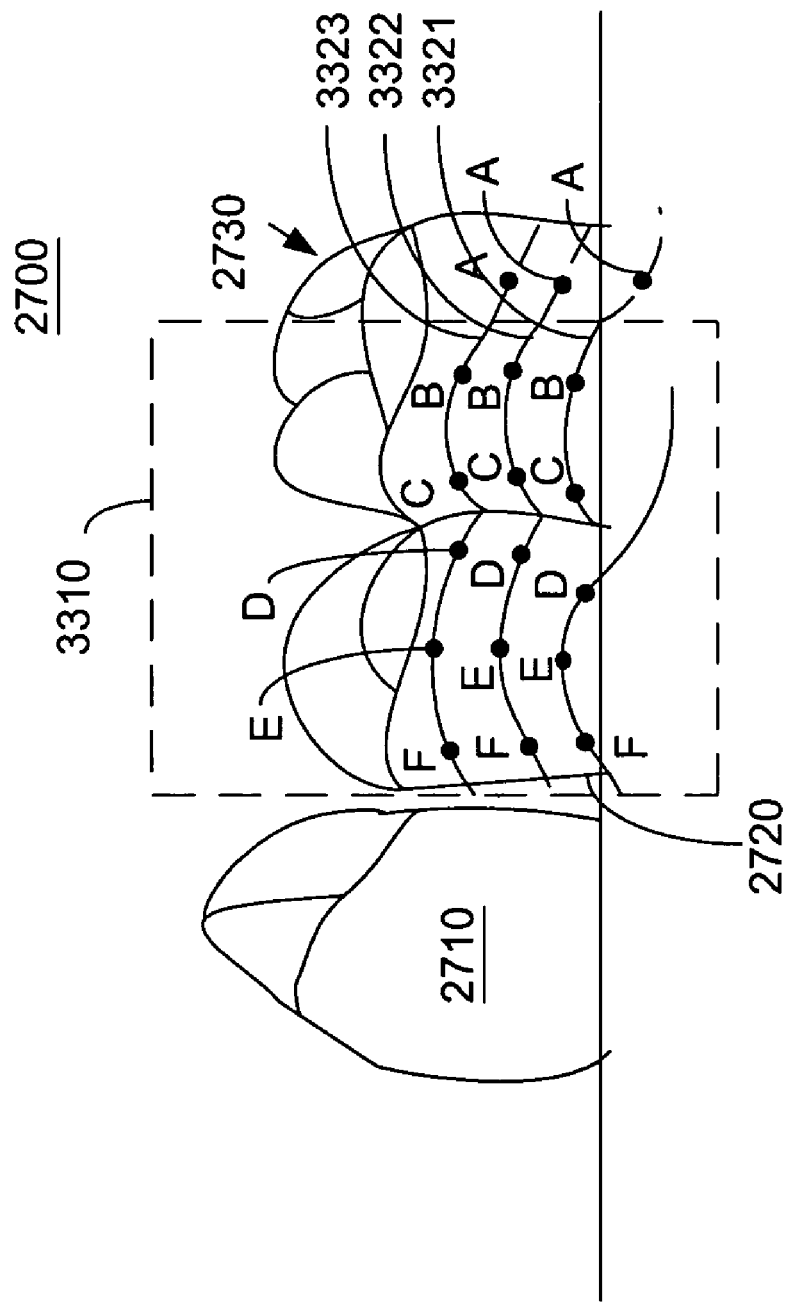

FIGS. 32 and 33 further illustrate the object 2700 being scanned from the FIG. 27 and FIG. 28 points-of-view respectively. In FIG. 32, the scan pattern includes scan lines 3221–3223. Any scan line portion outside the frame boundary 3210 is not capable of being properly scanned. Within the boundary 3210 each scan line, when sensed at the CCD (charge coupled diode) chip of the scanner, is converted to plurality of 2D points (cloud of data). Some or all points of a scan line can be used in accordance with the present invention. For example, every other, or every third point of a scan line can be used depending upon the desired resolution of a final 3D model. FIG. 32 illustrates four points (A–D) of each line being identified. A 2D coordinate value, such as an X-Y coordinate, is determined for each of these points.

In a specific embodiment of scanning, a scan rate of 1 to 20 frames per second is used. Greater scan rates can be used. In a specific embodiment, the scan rate is chosen to allow for real-time viewing of a three-dimensional image. The pulse time during which each frame is captured is a function of the speed at which the scanner is expected to be moving. For dentition structures, a maximum pulse width has been determined to be approximately 140 micro-second, although much faster pulse widths, i.e. 3 micro-seconds, are likely to be used.

In addition, in a specific embodiment, the teeth 2710–2730 will be coated with a substance that results in a surface that is more opaque than the teeth themselves.

In a specific embodiment, each point of the cloud of data will be analyzed during the various steps and functions described herein. In another embodiment, only a portion of the cloud of data will be analyzed. For example, it may be determined only every $3^{rd}$ or $4^{th}$ point needs to be analyzed for a desired resolution to be met. In another embodiment, a portion of the frame data can be a bounding box that is smaller than the entire frame of data such that only a specific spatial portion of the cloud of data is used for example, only a center portion of the cloud of data is included within the bounding box. By using a subset of the cloud of data, it is possible to increase the speed of various routines described herein.

FIG. 33 illustrates the object 2700 being scanned from the FIG. 28 point of view. As such, the viewed pattern including lines 3321–3323 are positioned differently on the teeth 2710–2730. In addition, the frame boundary 3310 has moved to include most of the tooth 2720.

Figure 34:
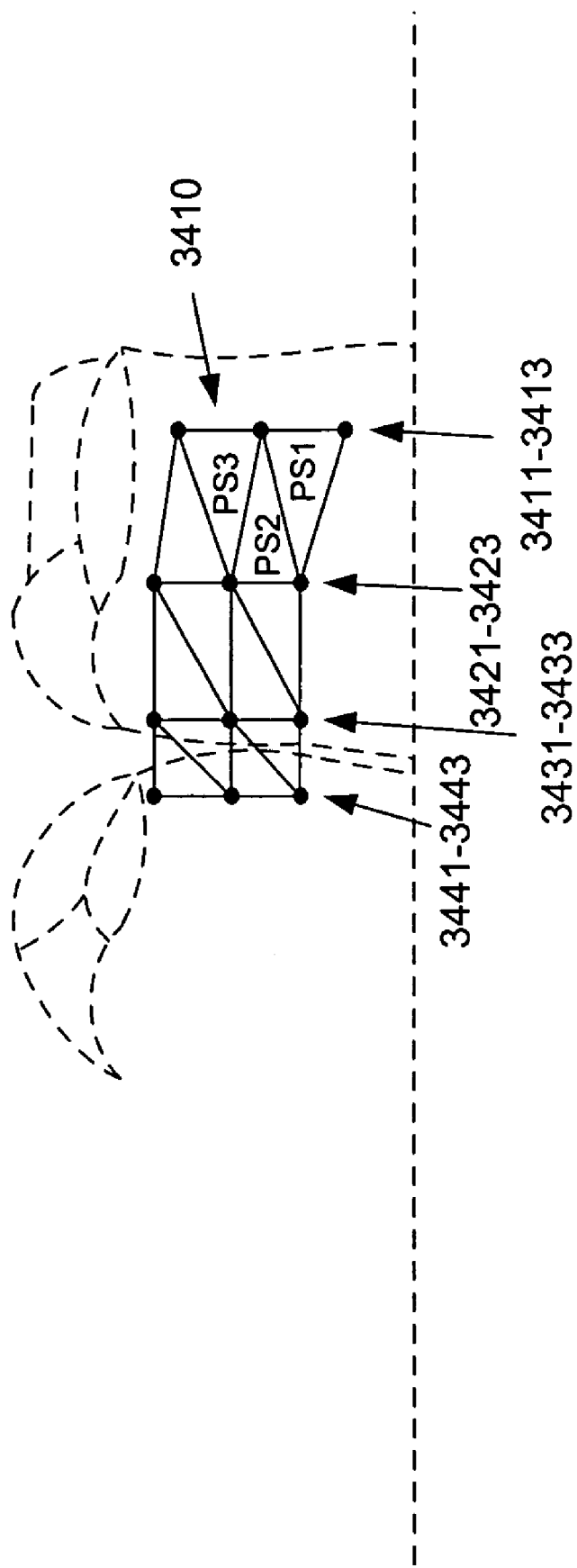
FIG. 34 illustrates primitive shapes for modeling a dentition object.

FIG. 34 illustrates another embodiment of a 3D frame model referred to herein as a 3D primitive model. A 3D primitive model includes a plurality of primitive shapes based upon the frame's 3D points. In the specific embodiment illustrated adjacent points from the 3D point model are selected to form triangles, including triangle PS1–PS3 as primitive shapes. Other implementations can use different or varied primitive shapes.

The use of primitive shapes to perform registration is advantageous over registration techniques that attempt to get the points of two point clouds as close as possible to each other, because using a primitive surface representation of one of the point clouds allows a lower resolution model to be used, resulting in a faster registration, without the disadvantage of undesirable offset error. For example, if a scan resolution of 1 mm is used for point-to-point registration, the best guaranteed alignment between two frames is 0.5 mm. This is due to the fact that the hand held scanner randomly captures which points of the surface are mapped. Using point-to-surface registration provides a more accurate result since the registration can occur to any point of the surface, not just the vertices.

At step 3103 of FIG. 31, a second 3D frame model is generated from the second frame of the cloud data. Depending upon the specific implementation, the second 3D frame model may be a point model or a primitive model.

At step 3104 a registration is performed between the first frame model and the second frame model to generate a cumulative model. "Registration" refers to the process of aligning the first model to the second model to determine a best fit by using those portions of the second model which overlap the first model. Those portions of the second model that do not overlap the first model are portions of the scanned object not yet mapped, and are added to the first model to create a cumulative model. Registration is better understood with reference to the method of FIG. 35.

Figure 35:
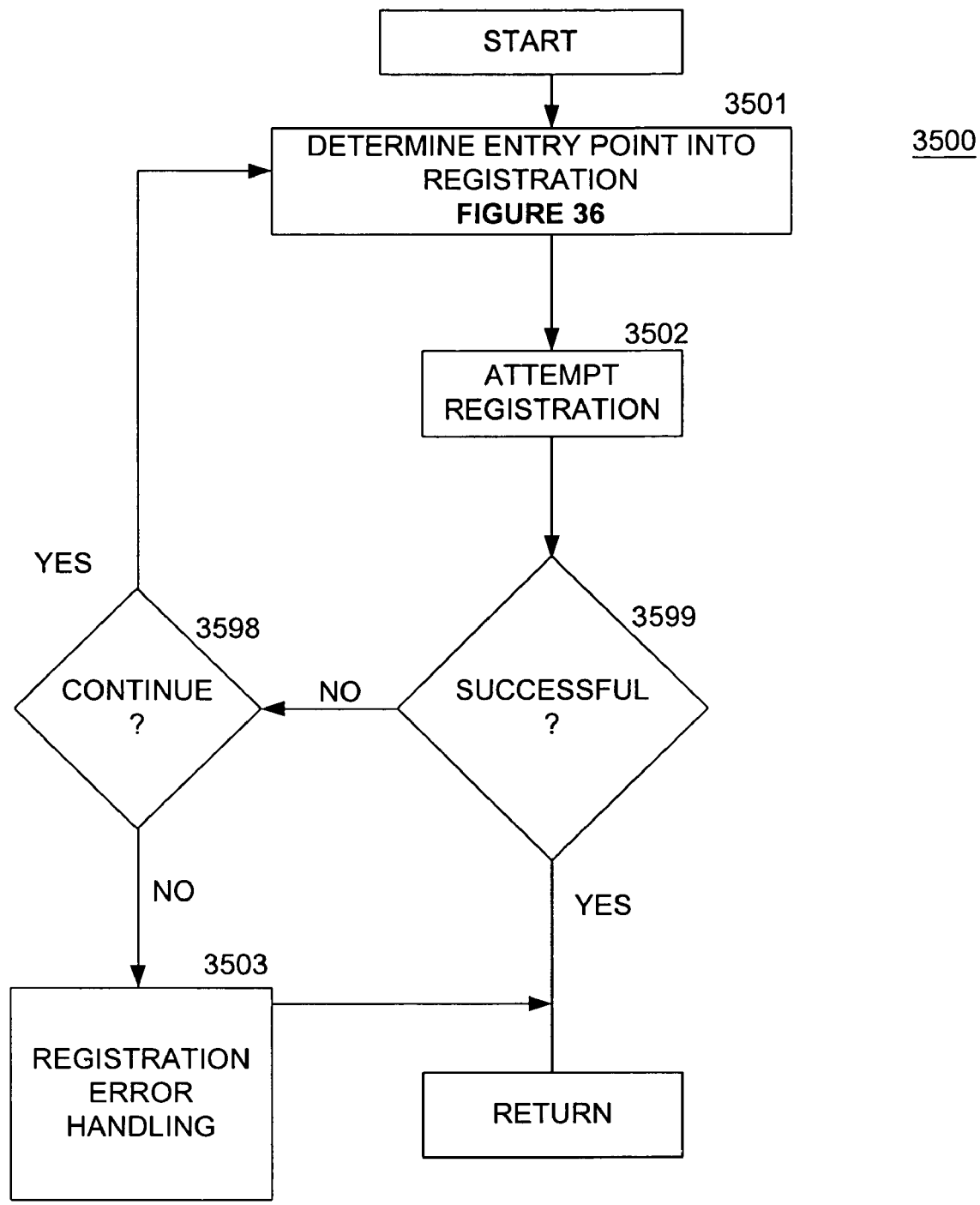
FIGS. 35 and 36 illustrate methods in accordance with a specific embodiment of the present invention.

FIG. 35 includes a registration method 3500 that, in a specific embodiment, would be called by one of the registration steps of FIG. 31. At step 3501 of FIG. 35 an entry point into registration is determined. The entry point into registration defines an initial guess of the alignment of the overlapping portions of the two models. The specific embodiment of choosing an entry point will be discussed in greater detail with reference to FIG. 36.

At step 3502, a registration of the two shapes is attempted. If an overlap is detected meeting a defined closeness of fit, or quality, the registration is successful. When the registration is successful the flow returns to the calling step of FIG. 31. When a registration is not successful the flow proceeds to the step 3598 were a decision whether to continue is made.

A decision to continue can be made based on a number of factors. In one embodiment, the decision to continue is made based upon the number of registration entry points that have been tried. If the decision at step 3598 is quit registration attempts, the flow proceeds to step 3503 where registration error handling occurs. Otherwise the flow continues at step 3501.

Figure 36:
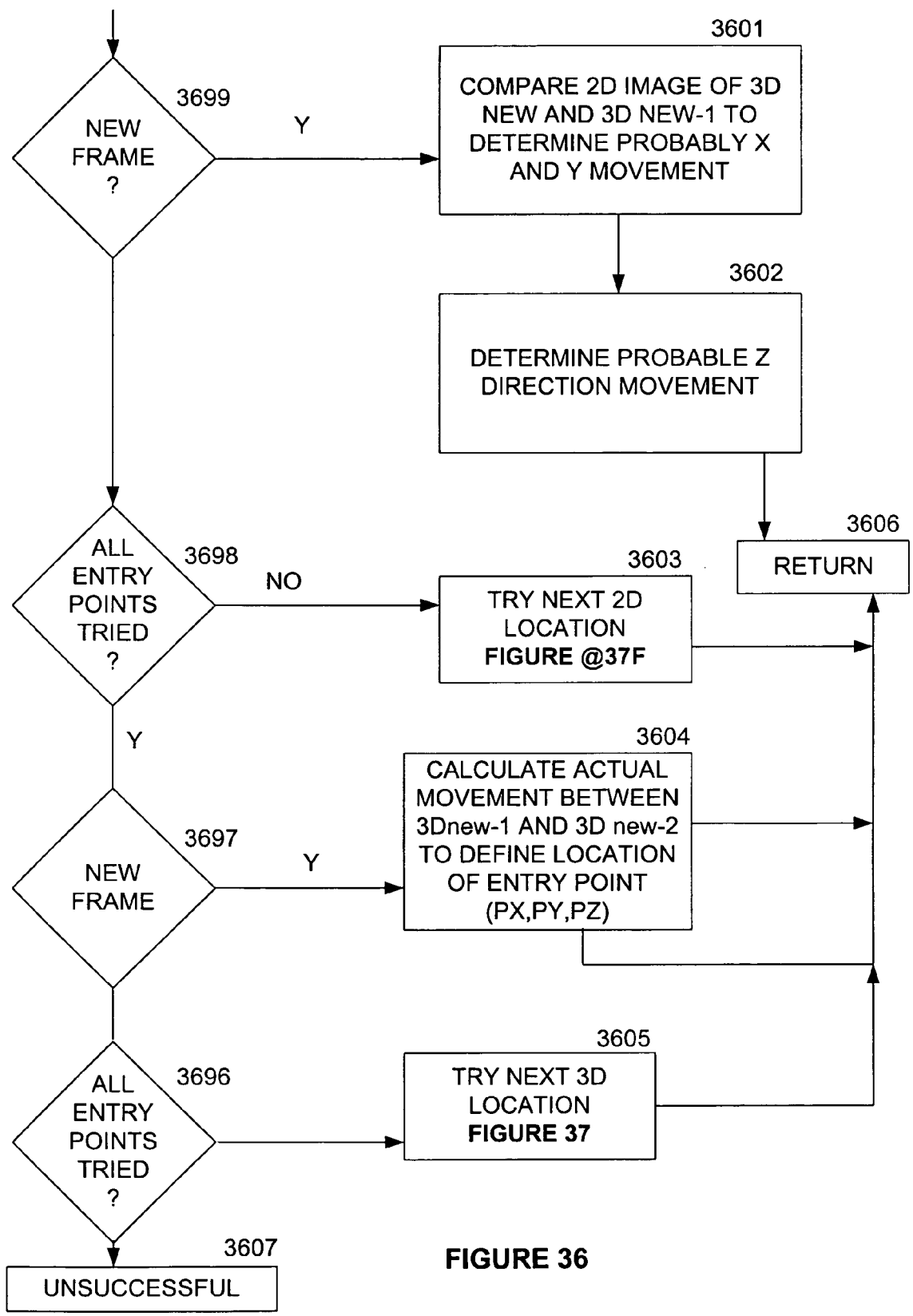

FIG. 36 illustrates a specific method for choosing a registration entry point. At step 3699 a determination is made whether this is the first entry point for a specific registration attempt of a new frame. If so the flow proceeds to step 3601, otherwise the flow proceeds to step 3698.

At step 3601 the X and Y components of the entry point are determined based upon two-dimensional analysis of the 2D cloud of data for each of the two frames. In a specific embodiment, the two-dimensional analysis performs a cross-correlation of the 2D images. These 2D images do not have to be from the 2D cloud of data, instead, data associated with a plain video image of the object, with no pattern, can be used for cross correlation. In this way, a probable movement of the scanner can be determined. For example, the cross-correlation is used to determine how the pixels have moved to determine how the scanner has probably been moved.

In another embodiment, a rotational analysis is possible, however, for a specific embodiment this is not done because it tends to be time consuming, and having the correct entry point in the X and Y-coordinate direction allows the registration algorithm described herein to handle rotations.

At step 3602, a probable movement in the Z direction is determined.

In one specific embodiment, the previous frame's Z-coordinate is used, and any change in the Z-direction is calculated as part of the registration. In another embodiment, a probable Z coordinate is calculated as part of the entry point. For example, the optical parameters of the system can "zoom" the second frame in relationship to the first one until the best fit is received. The zoom factor that is used for that could tell us how far the two surfaces are away from each other in Z. In a specific embodiment, the X, Y and Z coordinates can be aligned so that the Z-coordinate is roughly parallel to the view axis.

At step 3606, the entry point value is returned.

At step 3698 a determination is made whether all entry point variations have been tried for the registration steps 3601 and 3602. If not the flow proceeds to step 3603, otherwise the flow proceeds to step 3697.

Figure 37:
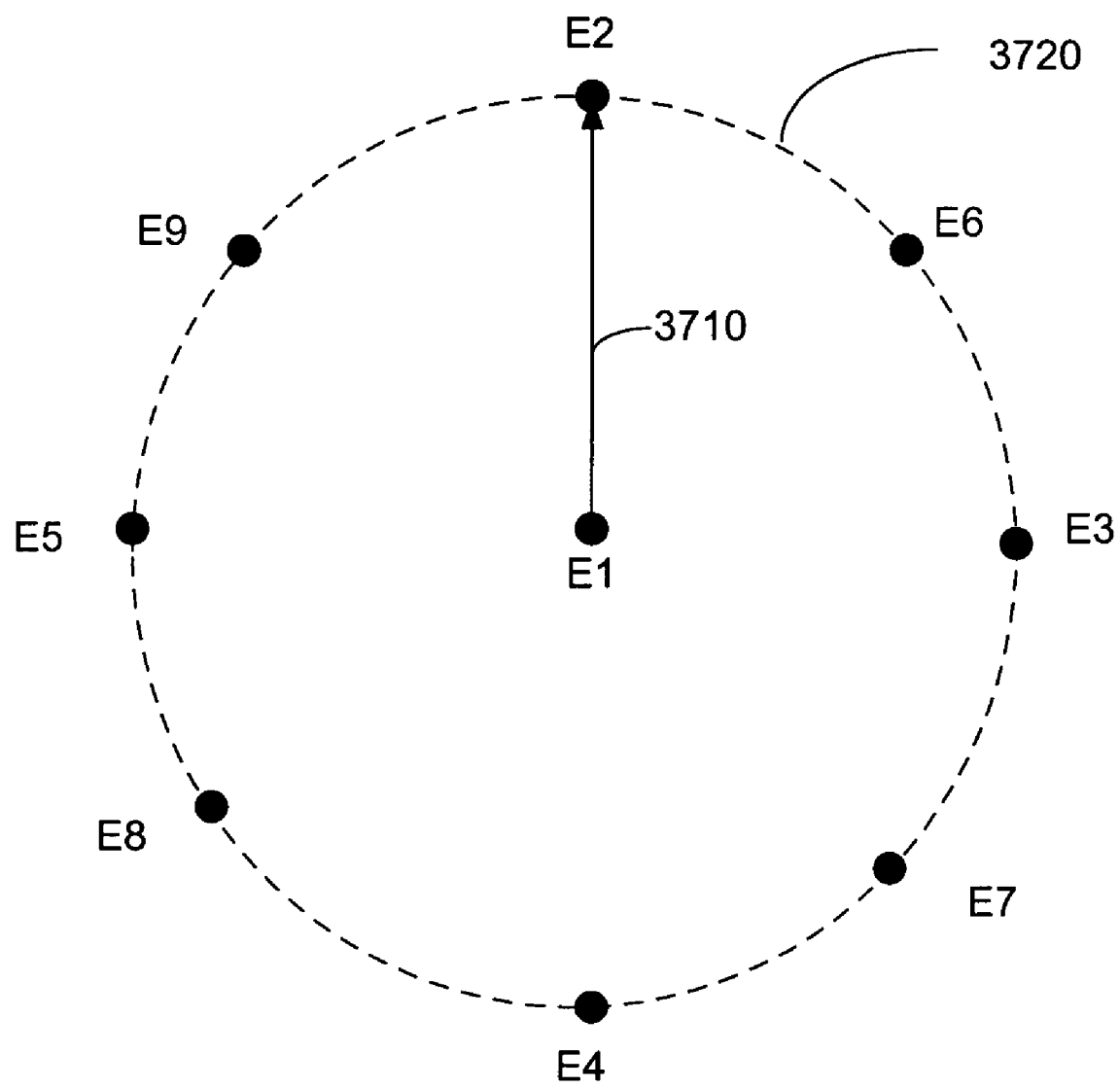
FIG. 37 illustrates a graphical representation of a method for selecting various entry points for registration in accordance with the present invention.

At step 3603 the next entry point variation is selected. FIG. 37 illustrates a specific method for selecting the registration entry point variations. Specifically, FIG. 37 illustrates the initial entry point E1 and subsequent entry points E2–E9. The entry points E2–E9 are selected sequentially in any predetermined order. The specific embodiment of FIG. 37 illustrates the registration entry points E2–E9 as various points of a circle 3720 having a radius 3710. In accordance with a specific embodiment, the dimensions of the entry point variations are two-dimensional, for example the X and Y dimensions. In other embodiments, the entry points can vary in three dimensions. Note that varying number of entry points, i.e. subsets of entry points, can be used to speed up the registration process. For example, single frame registration as used herein could use fewer than the nine entry points indicated. Likewise, cumulative registration, described herein, could benefit by using more than the nine points illustrated.

Returning to step 3698 of FIG. 36, the flow proceeds to step 3697 once all variations of the first identified entry point have been tried. At step 3697, all entry points associated with the first identified entry point have been tried, and it is determined whether a second identified entry point has been identified by step 3604. If not, flow proceeds to step 3604 where the second entry point is defined. Specifically, at step 3604 the scanner movement between two previous frame models is determined. Next, an assumption is made that the scanner movement is constant for at least one additional frame. Using these assumptions, the entry point at step 3604 is defined to be the location of the previous frame plus the calculated scanner movement. The flow proceeds to step 3606, which returns the entry point to the calling step of FIG. 35. In another embodiment, an assumption can be made that the direction of the scanner movement remained the same but that it accelerated at a difference rate.

If the second identified entry point of step 3604 has been previously determined, the flow from step 3697 will proceed to step 3696. At step 3696, a determination is made whether an additional registration entry point variation for the second identified entry point exists. If so, the flow proceeds to step 3605, otherwise the flow returns to the calling step of FIG. 35 at step 3607 and indicates that selection of a new entry point was unsuccessful. At step 3605 the next entry point variation of the second identified entry point is identified and the flow returns to the calling step of FIG. 35.

Different entry point routines can be used depending upon the type of registration being performed. For example, for a registration process that is not tolerant of breaks in frame data, it will be necessary to try more entry points before discarding a specific frame. For a registration process that is tolerant of breaks in frame data, simpler or fewer entry points can be attempted, thereby speeding up the registration process.

Returning to FIG. 31, at step 3105 the next 3D model portion is generated from the next frame's cloud of data.

At step 3106, registration is performed between the next 3D model portion and the cumulative model to update the cumulative model. In a specific implementation, the cumulative model is updated by adding all the new points from frame to the existing cumulative model to arrive at a new cumulative model. In other implementations, a new surface can be stored that is based on the 3D points acquired so far, thereby reducing the amount of data stored.

If all frames have been registered, the method 3100 is completed, otherwise the flow proceeds to steps 3105 through step 3199, until each frame's cloud of points has been registered. As result of the registration process described in method 3100, it is possible to develop a model for the object 2700 from a plurality of smaller frames, such as frames 3210 and 3310. By being able to register plurality of frames, highly accurate models of large objects can be obtained. For example, a model of a patients entire dentition structure, including gums, teeth, and orthodontic and prosthetic structures can be obtained. In another embodiment, a model of the patients face can be obtained.

Figure 38:
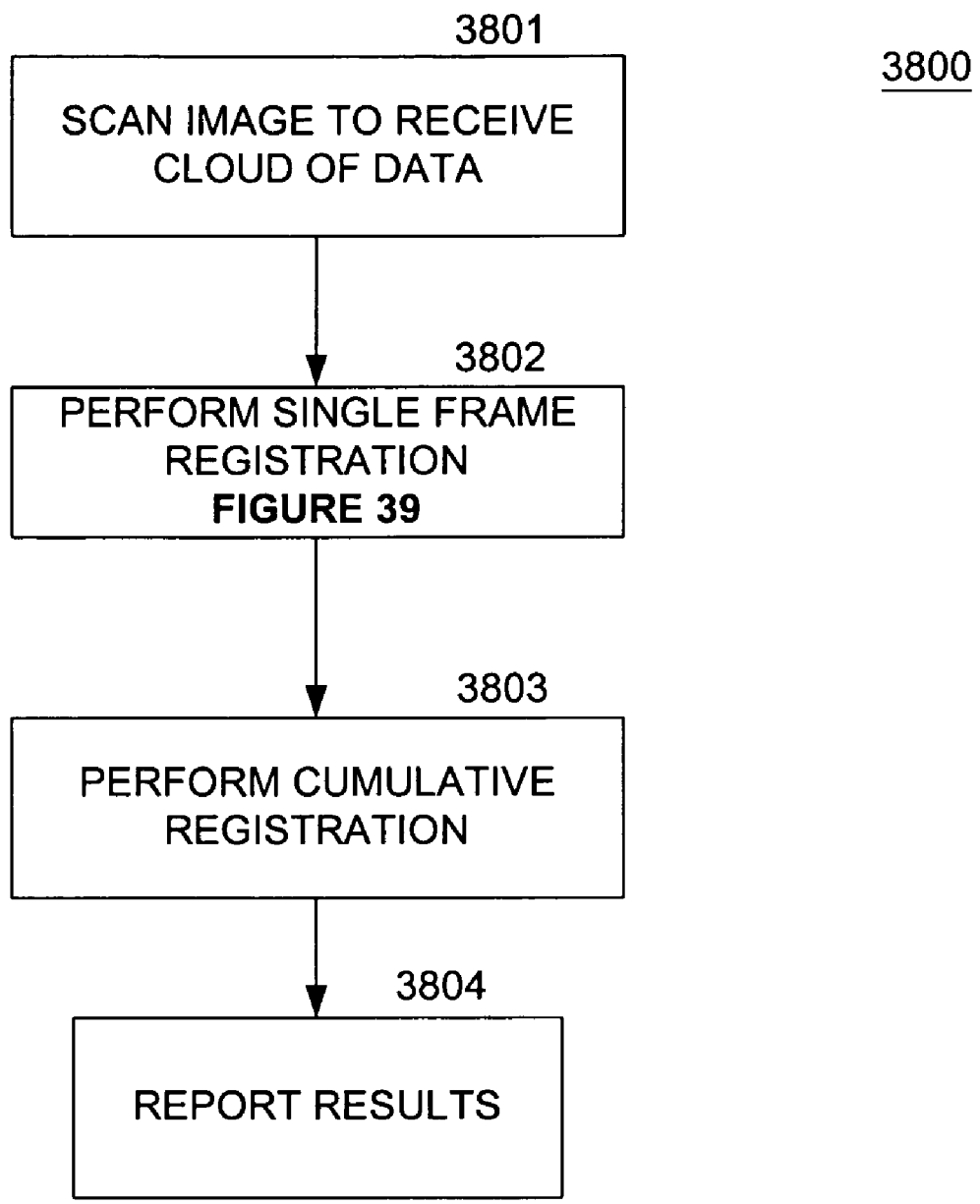
FIGS. 38–43 illustrate methods in accordance with a specific embodiment of the present invention.

FIG. 38 illustrates a method 3800, which is an alternate method of registering an object using a plurality of frames from a reference independent scanner. Specifically, at step 3801 the object is scanned to receive a cloud data for the object. As previously described, the cloud of data includes data from a plurality of frames, with each frame including a plurality of points.

At step 3802 a single frame registration is performed. A single frame registration performs a registration between adjacent frames of the scanned image without generating a cumulative model. Instead, in a specific implementation, a cumulative image of the single frame registration process is displayed. The image formed by the single frame registration process can be used to assist in the scanning process. For example, the image displayed as a result of the single frame registration, while not as accurate as a cumulative model, can be used by the scanner's operator to determine areas where additional scanning is needed.

The single frame registration process is such that any error introduced between any two frames is "extended" to all subsequent frames of a 3D model generated using single frame registration. However, the level of accuracy is adequate to assist an operator during the scanning process. For example, the registration results, which describe the movement from one frame to another, can be used as an entry point for the cumulative registration process. Single frame registration is discussed in greater detail with reference to FIG. 39.

At step 3803, a cumulative registration is performed. The cumulative registration creates a cumulative 3D model by registering each new frame into the cumulative model. For example, if 1000 individual frames were captured at step 3801 representing 1000 reference independent 3D model portions (frames), the cumulative registration step 3803 would combine the 1000 reference independent 3D model portions into a single cumulative 3D model representing the object. For example, where each of the 1000 reference independent 3D model portions represent a portion of one or more teeth, including frames 3210 and 3310 of FIGS. 32 and 33, the single cumulative 3D model will represent an entire set of teeth including teeth 2710–2730.

At step 3804, the results of the registration are reported. This will be discussed in further detail below.

Figure 39:
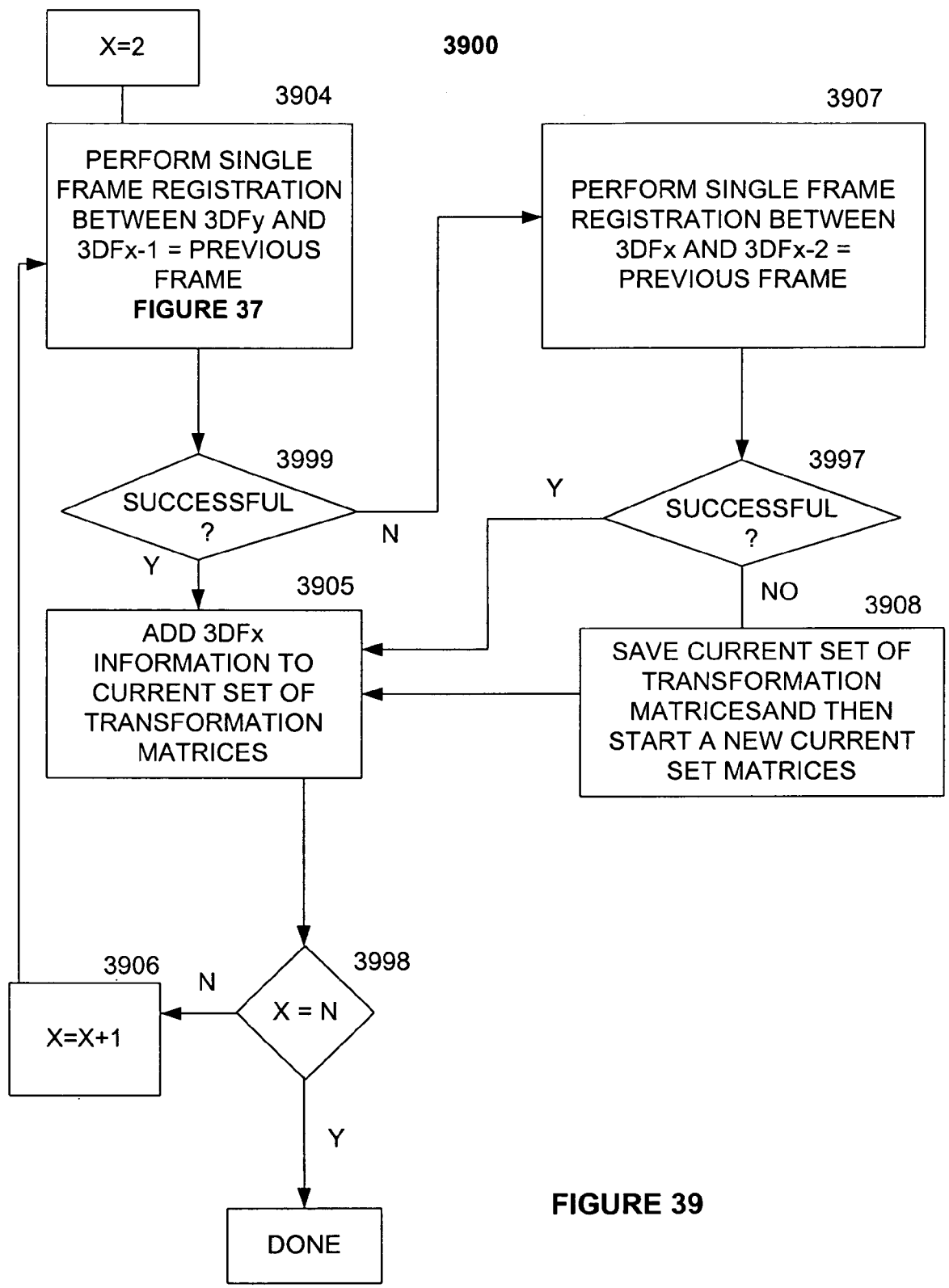

FIG. 39 describes a method 3900 that is specific to a single frame rendering implementation for step 3802 of FIG. 38. At step 3903 a variable x is set equal to 2.

At step 3904 a registration between the current frame (3DFx) and the immediately, or first, previous adjacent frame (3DFx-1) is performed. Registration between two frames is referred to as single frame registration. A specific embodiment of registration between two models is discussed in greater detail with reference to the method illustrated in FIG. 40.

Figure 40:
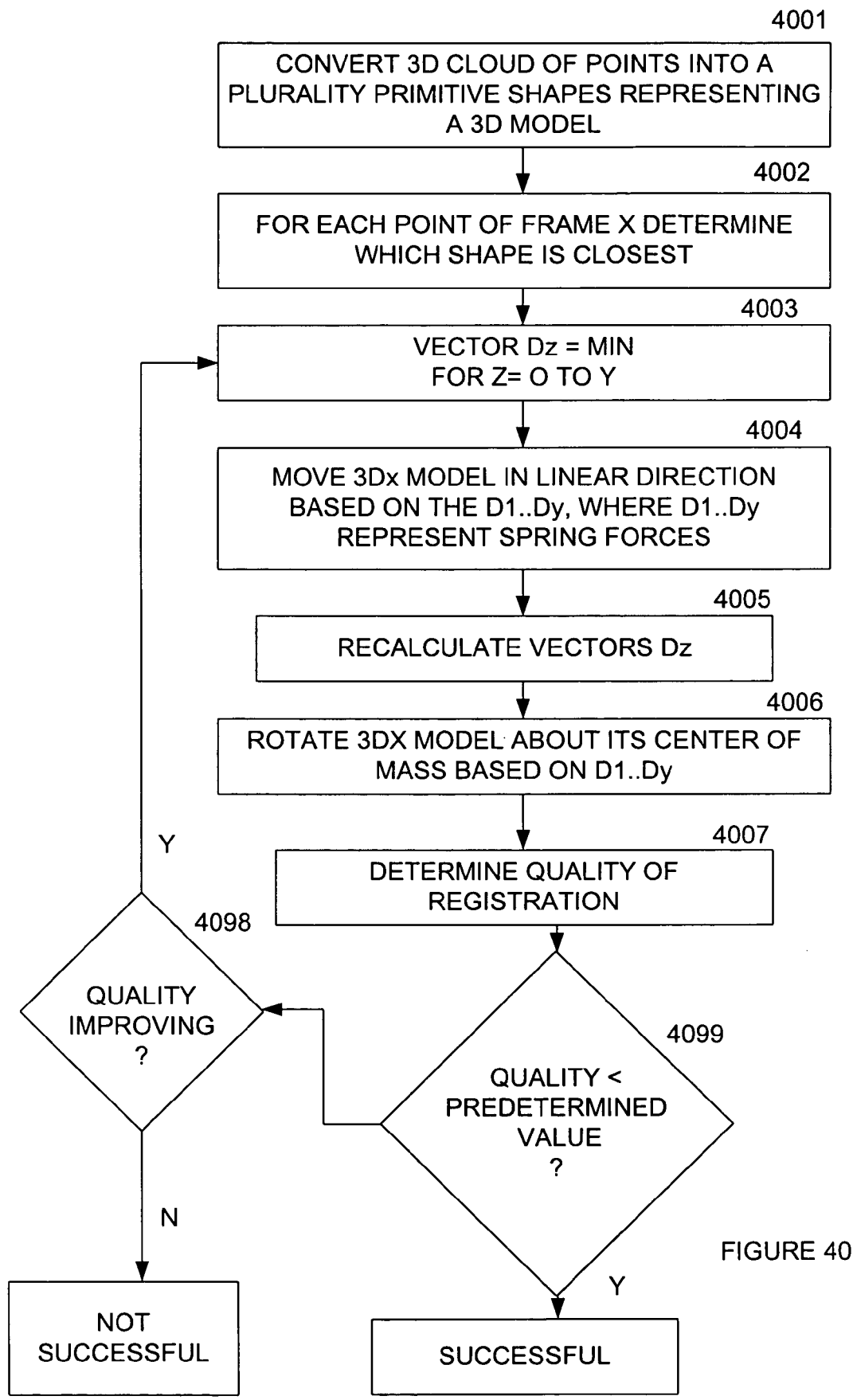

At step 3999 it is determined whether or not the single frame registration of step 3904 was successful. In a specific implementation, a registration method, such as the method of FIG. 40, provides a success indicator which is evaluated at step 3999. The flow proceeds to step 3905 when registration is successful, otherwise the flow proceeds to step 3907.

The flow proceeds to step 3905 when it is determined at step 3999 that the registration was successful. At step 3905 the current 3D frame (3DFx) is added to the current frame set of 3D frames. Note, that this set will generally be a set of transformation matrices. The current frame set of 3D frames is a sequential set of frames, where each frame in the sequence has a high degree of likelihood being successfully registered with [both] of its two adjacent frames. In addition, the newly registered frame can be displayed relative to the previous frame that is already being displayed.

At step 3998 a determination is made whether the variable x has a value equal to n, where n is the total number of frames to be evaluated. If x is equal to n, single frame registration is complete and the flow can return to FIG. 38 at step 3910. If x is less than n, single frame registration continues at step 3906, where x is incremented before proceeding to step 3904.

Returning to step 3999, the flow proceeds to step 3907 if the registration of step 3904 was not successful. At step 3907 a registration is attempted between current frame (3DFx) and the second previously adjacent frame (3DFx-2). Step 3997 directs the flow to step 3905 if the registration of step 3907 was successful. Otherwise, step 3997 directs the flow to step 3908, thereby indicating an unsuccessful registration of the current frame (3DFx).

When the current frame cannot be registered, step 3908 saves the current frame set, i.e. set of matrices, and a new current frame set is begun. Flow from step 3908 proceeds to step 3905 where the current frame is added to the current frame set, which was newly created at step 3908. Therefore, it is possible for the single frame registration step 3802 to identify multiple frames sets.

Generation of multiple frame sets during cumulative registration is not desirable due to the amount of intervention required to reconcile multiple cumulative models. However, breaks in single frame registration are generally acceptable because the purpose of single frame registration is to assist the operator and define entry points to cumulative registration. One method of dealing with breaks during single frame registration is to merely display the first frame after the break at the same location as the last frame before the break, thereby allowing the operator to continue to view an image.

In accordance with step 4001 of FIG. 40, a first model is a 3D primitive shape model, while the second model is a 3D point model. For reference purposes the primitive shapes in the first 3D model are referenced as S1 . . . Sn, where n is the total number of shapes in the first model; and, the points in the second 3D model are references as P1 . . . Pz, where z is the total number of points in the second model.

At step 4002, each individual point of the second model P1 . . . Pz is analyzed to determine a shape closest to its location. In a specific embodiment, for a point P1, the shape S1–Sn that is the closest to P1 is the shape having the surface location that is the closest to P1 than any other surface location of any other shapes. The shape closest to point P1 is referred to as Sc1, while the shape closest to point Pz is referred to as Scz.

In another embodiment, only points that are located directly above or below a triangle are associated to a triangle, and points that are not located directly above or below a triangle surface are associated to a line formed between two triangles, or a point formed by multiple triangles. Note that in the broad sense that the lines that form the triangles and the points forming the corner points of the triangles can be regarded as shapes.

At step 4003, vectors D1 ... Dz are calculated for each of the points P1 ... Pz. In a specific implementation, each vector, for example D1, has a magnitude and direction defined by the minimum distance from its corresponding point, for example P1, to the closest point of its closest shape, for example Sc1. Generally, only a portion of the points P1 ... Pz overlaps the cumulative image. The non-overlapping points, which are not needed for registration, have an associated vector having a comparatively large magnitude than an overlapping point, or may not reside directly above or below a specific triangle. Therefore, in a specific embodiment, only those vectors having a magnitude less than a predefined value (an epsilon value) are used for further registration.

In addition to eliminating points that are not likely to be overlapping points, the use of epsilon values can also be used to further reduce risks of decoding errors. For example, if one of the measuring lines of the pattern is misinterpreted to be a different line, the misinterpretation can result in a large error in the Z-direction. For a typical distance between adjacent pattern lines of approximately 0.3 mm and an angle of triangulation of approx. 13°; an error in the X-direction of 0.3 mm results in a three-dimensional transformation error of approx. 1.3 mm (0.3 mm/tan 13°) in the Z-direction. If the epsilon distance is kept below 0.5 mm we can be sure that there is no influence of surface areas further away from each other than 0.5 mm. Note that in a specific embodiment, the epsilon value is first selected to be a value greater than 0.5 mm, such as 2.0 mm, and after reaching a certain quality the value is reduced.

At step 4004, in a specific embodiment, the vectors D1 ... Dz are treated as spring forces to determine movement of the second 3D model frame. In a specific embodiment, the second 3D model is moved in a linear direction defined by the sum of all force vectors D1 ... Dz divided by the number of vectors.

At step 4005, the vectors D1 ... Dz are recalculated for each point of the second 3D model.

At step 4006, the vectors D1 ... Dz are treated as spring forces to determine movement of the second 3D model. For a specific embodiment of step 4004, the second 3D model frame is rotated about its center of mass based upon the vectors D1 ... Dz. For example, the second 3D model is rotated about its center of mass until the spring forces are minimized.

At step 4007, the quality of the registration is determined with respect to the current orientation of the second 3D model. One of ordinary skill in the art will recognize that various methods can be used to define the quality of the registration. For example, a standard deviation of the vectors D1 ... Dz having a magnitude less than epsilon can be used. In another embodiment quality is calculated using the following steps: square the distance of the vectors, sum the squared distances of all vectors within the epsilon distance, divide this sum by the number of vectors, and take the square root. Note, one of ordinary skill in the art will recognize that the vector values D1 ... Dz need to be recalculated after the rotation step 4006. In addition, one of ordinary skill in the art will recognize that there are other statistical calculations that can be used to provide quantitative values indicative of quality.

At step 4099, a determination is made whether the quality determined at step 4007 meets a desired quality level. If the quality is within a desired level, it indicates with a certain degree of confidence that a complete registration between the two frames models is achievable. By terminating the flow of method 4000 when a desired degree of quality is obtained, it is possible to quickly sort through all pairs of frames to provide an image to the user. By eliminating potential breaks in data at this point of the method, subsequent cumulative registration has a greater likelihood of producing a single cumulative model, as opposed to multiple segments of the cumulative model. If the current quality level meets the desired level the flow returns to the appropriate calling step with a successful indicator. If the current quality level does not meet desired level, the flow proceeds to step 4098.

It is determined at step 4098 whether the current quality of registration is improving. In a specific embodiment, this is determined by comparing the quality of the previous pass through the loop including step 4003 with the current quality. If the quality is not improving the flow returns to the calling step with an indication that the registration was not successful. Otherwise, the flow proceeds to step 4003.

Upon returning to step 4003, another registration iteration occurs, using the new frame location. Note that once the frame data has been scanned and stored there is no need to do the registration exactly in the order of scanning. Registration could start other way round, or use any other order that could make sense. Especially when scanning results in multiple passes there is already a knowledge of where a frame roughly belongs. Therefore, the registration of adjacent frames can be done independently of the order of imaging.

Figure 41:
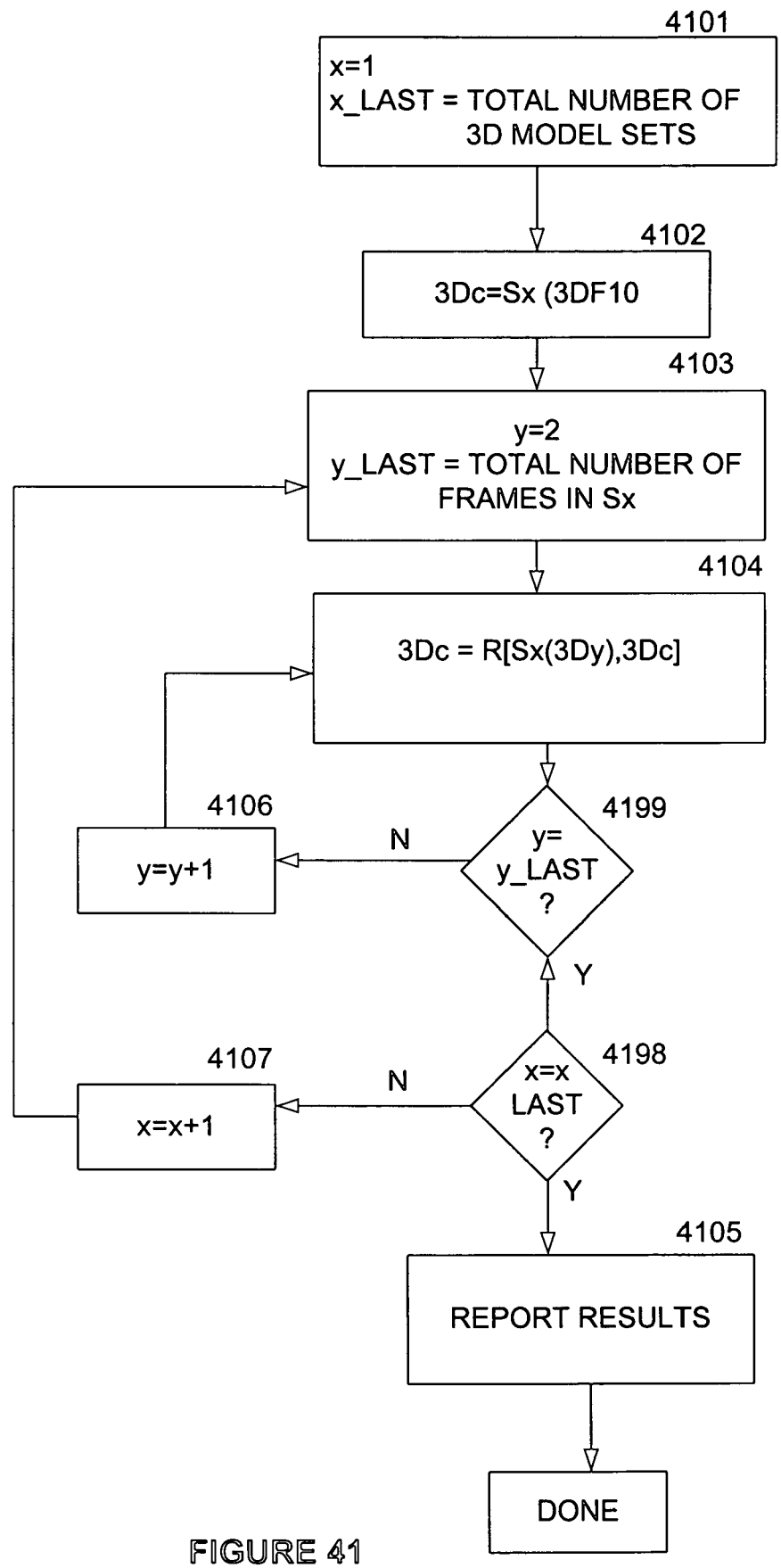

FIG. 41 illustrates a specific embodiment of a method 4100 for FIG. 38. Specifically, the method 4100 discloses a cumulative registration which attempts to combine all of the individual 3D frame models into a single cumulative 3D model.

Steps 4101–4103 are setup steps. At step 4101 a variable x is to set equal to 1, and a variable x_last defines the total number of 3D model sets. Note, the number of 3D model sets is based upon the step 3908 of FIG. 39.

At step 4102 a 3D cumulative model (3Dc) is initially defined to equal the first 3D frame of the current set of frames. The 3D cumulative model is modified to include that information from subsequent frame models that is not already represented by the 3D cumulative model.

At step 4103, Y is set equal to 2, and a variable Y_last is defined to indicate the total number of frames (3DF), or frame models, in the set Sx, where Sx represents the current set of frame models being registered.

At step 4104, the 3D cumulative model (3Dc) is modified to include additional information based upon the registration between the current 3D frame model being registered (Sx(3DFy)) and the 3D cumulative model (3DC). Note, in FIG. 41 the current 3D frame model is referenced as Sx(3Dy), where 3Dy indicates the frame model and Sx indicates the frame set. A specific embodiment for performing the registration of step 4104 is further described by the method illustrated in FIGS. 42–43.

At step 4199 it is determined whether the current 3D frame model is the last 3D frame model of the current step. In accordance with a specific implementation of FIG. 41, this can be accomplished by determining if the variable Y is equal to the value Y_last. When Y is equal to Y_last the flow proceeds to step 4198. Otherwise, the flow proceeds to step 4106, where Y is incremented, prior to returning to step 4104 for further registration of 3D frame models associated with current set Sy.

At step 4198 it is determined whether the current set of frames is the last set of frames. In accordance with the specific implementation of FIG. 41, this can be accomplished by determining if the variable x is equal to the value x_last. The flow proceeds to step 4105 when x is equal to a x_last. Otherwise, the flow proceeds to step 4107, where x is incremented, prior to returning to step 4103 for further registration using the next set.

All frames of all sets have been registered when the flow reaches step 4105. Step 4105 reports results of the registration of the method 4100, as well as any other cleanup operations. For example, while ideally the method 4100 results in a single 3D cumulative model in reality multiple 3D cumulative models can be generated (see discussion at step 4207 of FIG. 43). When this occurs step 4105 can report the resulting number of 3D cumulative models to the user, or to a subsequent routine for handling. As a part of step 4105, the user can have an option to assist in registering the multiple 3D models to each other. For example, if two 3D cumulative models are generated, the user can manipulate the 3D cumulative models graphically to assist identification of entry point, which can be used for performing a registration between the two 3D cumulative models.

In accordance with another embodiment of the present invention, a second cumulative registration process can be performed using the resulting matrices from the first cumulative registration as entry points for the new calculations. In one embodiment, when the process encounters a point where frame(s) could not be successfully registered in the first attempt, an enlarged number of entry points can be used, or a higher percentage of points can be used.

Figure 42:
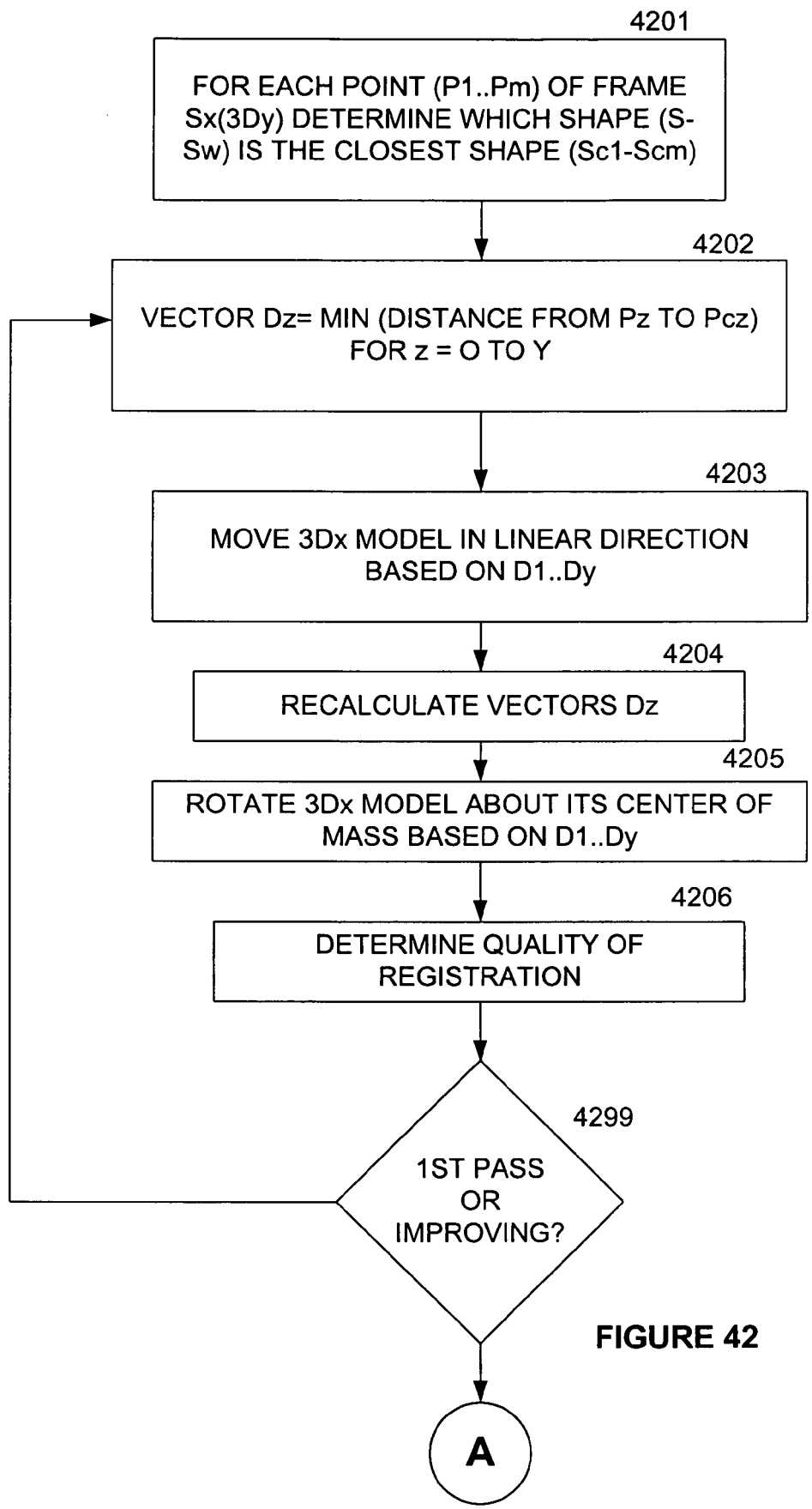
Figure 43:
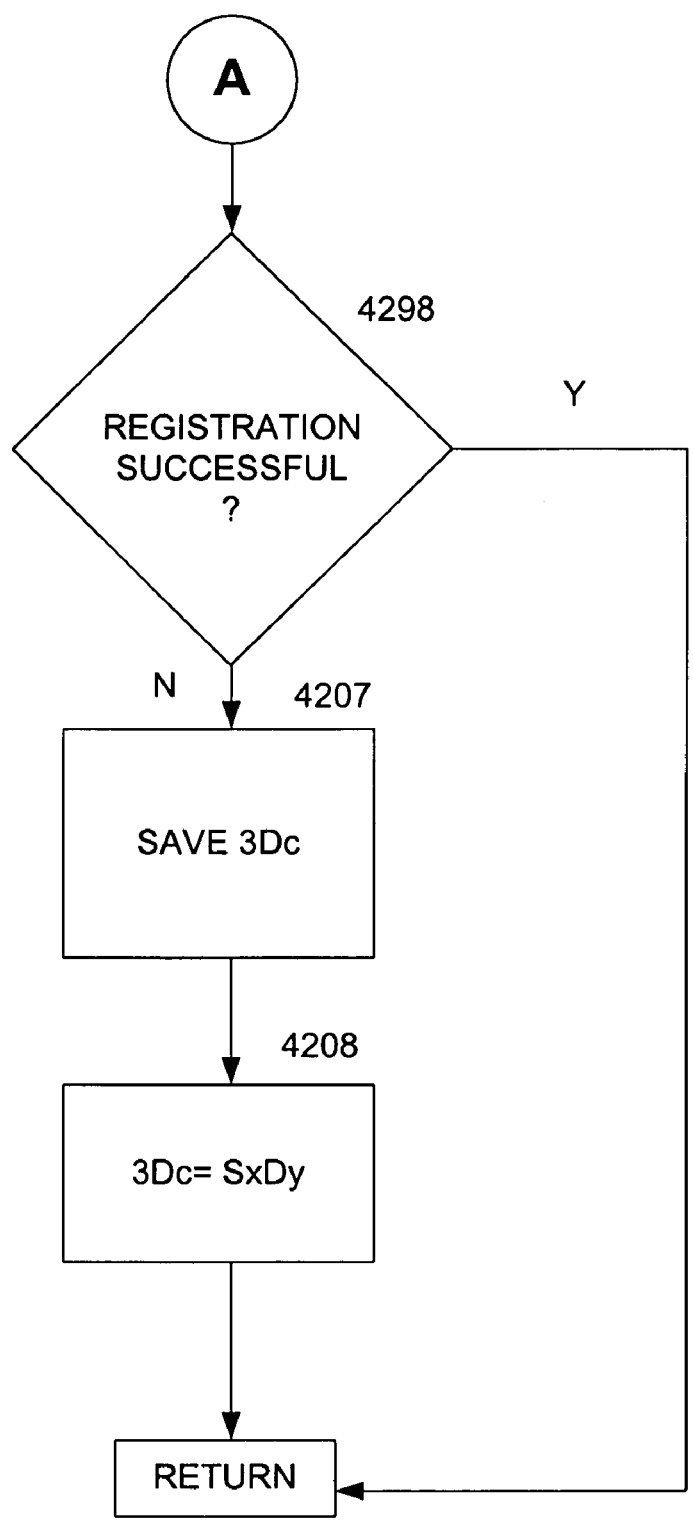

FIGS. 42–43 illustrate a specific embodiment of registration associated with step 4104 of FIG. 41.

Step 4201 is similar to step 4002 of FIG. 40, where each point (P1 . . . Pm) of the current frame Sx(3Dy) is analyzed to determine the shape of the cumulative model that is the closest shape.

Step 4202 defines vectors for each point of the current frame in a manner similar to that previously described with reference to step 4003 of FIG. 40.

Steps 4203 through 4206 move the current 3D frame model in the manner described at steps 4004–4006 of FIG. 40, where the first model of method 4000 is the cumulative model and a second model of method 4000 is the current frame.

At step 4299 a determination is made whether the current pass through registration steps 4202–4206 has resulted in an improved alignment between the cumulative model and the current frame model. One method of determining quality improvement is to compare a quality value based on the current position of the model register to the quality value based on the previous position of the model. As previously discussed with reference to FIG. 40, the quality value can be determined using the standard deviation, or other quality calculation based on the D vectors. Note, by default, a first pass through steps 4202–4206 for each model 3Dy results in an improved alignment. If an improved alignment has occurred, the flow returns to step 4202, otherwise the flow proceeds to step 4298 of FIG. 43.

Note that the flow control for the cumulative registration method of FIG. 42 is different than the flow control for the single frame registration method of FIG. 40. Specifically, the cumulative flow continues until no improvement in quality is realized, while the single frame flow stops once a specified quality is reached. Other embodiments of controlling the flow within the registration routines are anticipated.

In an alternate flow control embodiment, the registration iteration process continues as long as a convergence criteria is met. For example, the convergence criteria is considered met as long as an improvement in quality of greater than a fixed percentage is realized. Such a percentage can be in the range of 0.5–10%.

In another embodiment, even once a specific first criteria is met, such as convergence or no improvement in quality, additional stationary iterations can be used. A stationary iteration is a pass through the registration routine, once the quality level has stopped improving, or has met a predefined criteria. In a specific implementation, a number of stationary iterations can be fixed. For example, 3 to 10 additional iterations can be specified.

At step 4298 it is determined whether or not the current registration is successful. In a specific implementation success is based solely upon whether the calculated quality value of the current model placement meets a predefined criteria. If so, the registration has been successful and the routine 4200 returns to the calling step. If the criteria is not met, the flow proceeds to step 4207.

At step 4207, it has been determined that current frame model cannot be successfully registered into the cumulative 3D model. Therefore, the current cumulative 3D model is saved, and a new cumulative 3D model is started having the current frame. As previously described, because a new 3D cumulative model has been started, the current 3D frame model, which is a point model, is converted to a primitive model before returning to the calling step.

Many other embodiments of the present invention exist. For example, the movement of the frame during steps 4004, 4006, 4203, and 4205 may include an acceleration, or over movement, component. For example, an analysis may indicate that a movement in a specific direction needs to be 1 mm. However, to compensate for the size of the sample being calculated or other factors, the frame can be moved by 1.5 mm, or some other scaled factor. Subsequent movements of the frame can use a similar or different acceleration factor. For example, a smaller acceleration value can be used as registration progresses. The use of an acceleration factor helps compensate for local minima, which result when no overlapping features happen to align. When this happens, a small movement value can result in a lower quality level. However, by using acceleration it is more likely that the misalignment can be overcome. Generally, acceleration can be beneficial to overcome "bumpiness" in a feature.

It should be understood that the specific steps indicated in the methods herein, and/or the functions of specific modules herein, may generally be implemented in hardware and/or software. For example, a specific step or function may be performed using software and/or firmware executed on one or more a processing modules.

Typically, systems for scanning and/or registering of scanned data will include generic or specific processing modules and memory. The processing modules can be based on a single processing device or a plurality of processing devices. Such a processing device may be a microprocessor, microcontroller, digital processor, microcomputer, a portion of a central processing unit, a state machine, logic circuitry, and/or any device that manipulates the signal.

The manipulation of these-signals is generally-based upon operational instructions represented in a memory. The memory may be a single memory device or a plurality of memory devices. Such a memory device (machine readable media) may be a read only memory, a random access memory, a floppy disk memory, magnetic tape memory, erasable memory, a portion of a system memory, any other device that stores operational instructions in a digital format. Note that when the processing module implements one or more of its functions, it may do so where the memory storing the corresponding operational instructions is embedded within the circuitry comprising a state machine and/or other logic circuitry.

The present invention has been described with reference to specific embodiments. In other embodiments, more than two registration processes can be used. For example, if the cumulative registration process has breaks resulting in multiple cumulative models, a subsequent registration routine can be used to attempt registration between the multiple cumulative models.

One of ordinary skill in the art will recognize that the present invention is advantageous over the prior art, in that a reference independent scanner is disclosed that in a specific embodiment incorporates variable identifiers in a direction orthogonal to a projection/view plane. By providing variables in a direction orthogonal to the projection/view plane, the distortion of these variables, which is less than distortion parallel to the projection/view plane, does not prohibit identification of specific shapes. As a result, greater accuracy, of mapping of objects can be obtained.

We claim:

1. A method of mapping a surface, the method comprising:
    a) using a single movable reference independent scanner, projecting an image along a projection axis onto a surface to provide a surface image, wherein said image includes a variable feature which varies in a direction substantially orthogonal to a plane formed by the projection axis and a point of a view axis;
    b) receiving a representation of said surface image along said view axis;
    c) determining a location at a point of said surface image based at least partially upon said variable feature of the representation of said surface image;
    d) repeating steps a), b), and c) thereby acquiring a series of frames wherein each of said frames comprises a plurality of said location points;
    e) performing a single frame registration of said frames;
    f) displaying the surface mapped from said single frame registration, including breaks in said mapped surface, thereby enabling the scanner's operator in determining the areas where additional scanning is needed;
    g) repeating steps a)–f) until the entire surface is mapped using said single frame registration;
    h) performing a cumulative registration of said frames, wherein said cumulative registration may result in multiple cumulative models of said mapped surface; and
    i) when said multiple cumulative models result, an user manipulating said multiple cumulative models graphically thereby assisting in said cumulative registration.

2. The method of claim 1, wherein the image is a predefined pattern.

3. The method of claim 2, wherein the predefined pattern includes
    a first image portion having a first feature that includes at least the location at the point of the surface, and a second feature which includes at least a portion of the variable feature;
    a second image portion having a third feature, and a fourth feature; and
    the step of determining further includes using the second feature to identify the first feature.

4. The method of claim 3, wherein the first feature does not vary in a direction orthogonal to the plane, and the third feature does not vary in a direction orthogonal to the plane and is substantially parallel to the first feature.

5. The method of claim 4 wherein the second feature includes a first color sequence and the fourth feature has a second color sequence which is different than the first color sequence.

6. The method of claim 4 wherein the predefined pattern includes a third feature having a third color which comprises a plurality of colors.

7. The method of claim 6, further including the step of:
    determining a color of the surface based upon the third feature; and
    wherein the step of projecting includes the sub step of selecting the first color and the second color based upon a viewed image of the third feature.

8. The method of claim 3, wherein the second feature includes a plurality of components having a first sequence of thicknesses, and the fourth feature includes a plurality of components having a second sequence of thicknesses which is not equal to the first sequence of thickness.

9. The method of claim 3, wherein the second feature varies in a first manner, and the fourth feature varies in a second manner which is not the same as the first manner.

10. The method of claim 1, wherein the variable feature is a unique pattern.

11. The method of claim 1, wherein the variable feature is color.

12. The method of claim 1, wherein the variable feature is line thickness.

13. The method of claim 1, wherein the variable feature has a portion which is projected parallel to the plane.

14. The method of claim 1, wherein the image is a static image.

15. The method of claim 1, wherein the location is a relative location.

16. The method of claim 1, wherein the step of determining a location includes determining the location by quantifying the location.

17. A method of mapping a surface, the method comprising:
    a) using a single movable reference independent scanner, projecting an image along a projection axis onto a surface to provide a surface image, wherein said image includes a pattern, said pattern having a plurality of first features and a plurality of second features, wherein each of the plurality of said second features are uniquely identifiable independent of the topology of said surface;
    b) receiving a representation of said surface image along said view axis;
    c) determining a specific feature of the plurality of said first features based upon the plurality of said second features from said representation of said surface image;
    d) calculating a relative location of a point of said surface image based upon said specific feature;
    e) repeating steps a), b), c) and d) thereby acquiring a series of frames wherein each of said frames comprises a plurality of said location points;
    f) performing a single frame registration of said frames;
    g) displaying the surface mapped from said single frame registration, including breaks in said mapped surface, thereby enabling the scanner's operator in determining the areas where additional scanning is needed;
    h) repeating steps a)–g) until the entire surface is mapped using said single frame registration;
    i) performing a cumulative registration of said frames, wherein said cumulative registration may result in multiple cumulative models of said mapped surface; and j) when said multiple cumulative models result an user manipulating said multiple cumulative models graphically thereby assisting in said cumulative registration.

18. The method of claim 17, wherein the step of projecting further includes the plurality of first features being substantially parallel first features.

19. The method of claim 17, wherein the step of projecting further includes each of the plurality of second features being uniquely identifiable based on color.

20. The method of claim 19, wherein the step of projecting further includes each of the plurality of second features being uniquely identifiable based on color, wherein the color is a color associated with white light.

21. The method of claim 17, wherein the step of projecting further includes each of the plurality of second features being uniquely identifiable based on intensity.

22. The method of claim 17, wherein the step of projecting further includes each of the plurality of second features being uniquely identifiable based on unique patterns.

23. A method for scanning an object, the method comprising the steps of:
   a) using a single movable reference independent scanner, projecting an image along a projection axis onto a surface to provide a surface image, wherein said image includes a plurality of discrete shapes comprising a first discrete shape and a second discrete shape;
   b) projecting a first encoding feature relative to said first discrete shape;
   c) receiving a representation of said surface image along said view axis including said first encoding feature;
   d) identifying representation of said first discrete shape based upon said first encoding feature from said representation of said surface image;
   e) determining a location of a specific point of said surface image based upon said representation of said first discrete shape;
   f) repeating steps a), b), c), d) and e) thereby acquiring a series of frames wherein each of said frames comprises a plurality of said location points;
   g) performing a single frame registration of said frames;
   h) displaying the surface mapped from said single frame registration, including breaks in said mapped surface, thereby enabling the scanner's operator in determining the areas where additional scanning is needed;
   i) repeating steps a)–h) until the entire surface is mapped using said single frame registration;
   j) performing a cumulative registration of said frames, wherein said cumulative registration may result in multiple cumulative models of said mapped surface; and
   k) when said multiple cumulative models result, an user manipulating said multiple cumulative models graphically thereby assisting in said cumulative registration.

24. The method of claim 23 further comprising the step of: projecting a second encoding feature relative to the second discrete shape.

25. The method of claim 23, wherein the step of projecting the plurality of discrete shapes includes projecting the first and second discrete shapes in a manner that allows the first and second discrete shapes to distort when projected upon the object during the step of determining the first discrete shape; and wherein the steps of projecting the first encoding feature includes projecting the first encoding feature in a manner that substantially precludes distortion of the first and second encoding features.

26. An apparatus for scanning an object, the system comprising:
   a single movable reference independent scanner;
   a data processor for executing instructions; and
   a plurality of instructions capable of being executed on said data processor to execute the following operations:
      a) projecting an image along a projection axis onto a surface to provide a surface image, wherein said image includes a plurality of discrete shapes for scanning an object, wherein the plurality of said discrete shapes include a first discrete shape and a second discrete shape;
      b) projecting a first encoding feature relative to the first discrete shape;
      c) receiving a representation of said surface image along said view axis including said first encoding feature;
      d) identifying representation of said first discrete shape based upon said first encoding feature from said representation of said surface image;
      e) determining a location of a specific point of said surface image based upon said representation of said first discrete shape;
      f) repeating steps a), b), c), d) and e) thereby acquiring a series of frames wherein each of said frames comprises a plurality of said location points;
      g) performing a single frame registration of said frames;
      h) displaying the surface mapped from said single frame registration, including breaks in said mapped surface, thereby enabling the scanner's operator in determining the areas where additional scanning is needed;
      i) repeating steps a)–h) until the entire surface is mapped using said single frame registration;
      j) performing a cumulative registration of said frames, wherein said cumulative registration may result in multiple cumulative models of said mapped surface; and
      k) when said multiple cumulative models result, an user manipulating said multiple cumulative models graphically thereby assisting in said cumulative registration.

27. The method of claim 1, wherein said movable reference independent scanner comprises a hand-held scanner.

28. The method of claim 17, wherein said movable reference independent scanner comprises a hand-held scanner.

29. The method of claim 23, wherein said movable reference independent scanner comprises a hand-held scanner.

30. The apparatus of claim 26, wherein said movable reference independent scanner comprises a hand-held scanner.

* * * * *